United States Patent [19]

Ashton et al.

[11] Patent Number: 5,312,820
[45] Date of Patent: May 17, 1994

[54] SUBSTITUTED CARBAMOYL AND OXYCARBONYL DERIVATIVES OF BIPHENYLMETHYLAMINES

[75] Inventors: Wallace T. Ashton, Clark; Linda L. Chang, Wayne; William J. Greenlee, Teaneck; Steven M. Hutchins, Iselin; Ralph A. Rivero, Tinton Falls, all of N.J.

[73] Assignee: Merck & Co., Inc., Rahway, N.J.

[21] Appl. No.: 917,642

[22] Filed: Jul. 17, 1992

[51] Int. Cl.$^5$ .................. A61K 31/47; A61K 31/415; A61K 31/34; A61K 31/535; A61K 31/54; A61K 31/17; A61K 31/27; C07C 275/28; C07D 207/16; C07D 265/36; C07D 275/04; C07D 295/22

[52] U.S. Cl. .................. 514/227.5; 514/230.5; 514/234.8; 514/297; 514/312; 514/313; 514/346; 514/349; 514/381; 514/394; 514/418; 514/419; 514/450; 514/471; 514/596; 514/597; 514/598; 544/52; 544/105; 544/354; 544/355; 544/356; 549/401; 549/483; 549/484; 549/487; 546/102; 546/103; 546/104; 546/105; 546/106; 546/153; 546/159; 546/163; 546/168; 546/169; 546/292; 548/251; 548/306.4; 548/307.4; 548/361.5; 548/362.1; 548/483; 560/27; 564/48; 564/49; 564/50; 564/51; 564/52

[58] Field of Search ........ 546/168, 169, 153, 102-106, 546/192; 564/48, 49, 52, 50, 51; 560/27; 544/283, 52, 105, 354-356; 548/251, 362.1, 361.5, 483, 306.4, 307.4; 514/234.8, 238.5, 227.5, 297, 312, 313, 381, 346, 347, 394, 403, 448, 417, 471, 450, 596, 597, 598; 549/401, 483, 484, 487

[56] References Cited

U.S. PATENT DOCUMENTS

| | | | |
|---|---|---|---|
| 3,910,911 | 10/1975 | Ishizumi et al. | 564/49 X |
| 4,410,697 | 10/1983 | Torok et al. | 564/49 X |
| 4,422,871 | 12/1983 | Schirmer et al. | 564/49 X |
| 5,157,040 | 10/1992 | Greenlee et al. | 546/168 |

FOREIGN PATENT DOCUMENTS

| | | | |
|---|---|---|---|
| 0041145 | 12/1981 | European Pat. Off. | 564/49 |
| 0335374 | 10/1989 | European Pat. Off. | 564/52 |
| 0365484 | 4/1990 | European Pat. Off. | 564/49 |
| 443983 | 8/1991 | European Pat. Off. | 546/168 |
| 490820 | 6/1992 | European Pat. Off. | 546/168 |

*Primary Examiner*—Floyd D. Higel
*Attorney, Agent, or Firm*—Robert T. North; Joseph F. DiPrima

[57] ABSTRACT

Carbamoyl and oxycarbonyl derivatives of biphenylmethylamines of structure I are angiotensin-II antagonists with balanced $AT_1$ and $AT_2$ activity useful in the treatment of hypertension and related disorders and ocular hypertension.

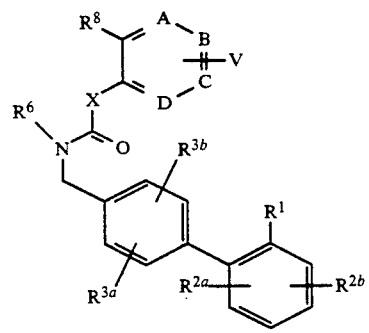

where X is —O— or —N($R^7$)—.

22 Claims, No Drawings

SUBSTITUTED CARBAMOYL AND OXYCARBONYL DERIVATIVES OF BIPHENYLMETHYLAMINES

SUMMARY OF THE INVENTION

This invention is concerned with novel substituted carbamoyl and oxycarbonyl derivatives of biphenylmethylamines of structural formula I

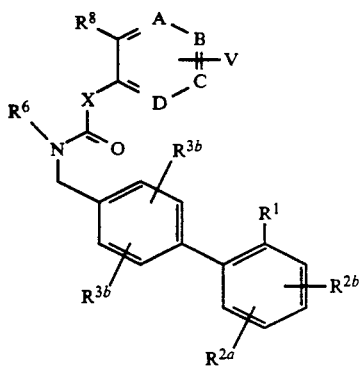

wherein X is —O— or —N(R$^7$)— and A, B, C, D, are —N= or —CH=, which demonstrate balanced AT$_1$-/AT$_2$ angiotensin II (A-II) antagonist activity, useful in the treatment of ocular hypertension and glaucoma resulting therefrom and hypertension of the cardiovascular system and disorders associated therewith, especially acute and chronic congestive heart failure and angina.

This invention is also concerned with: processes for preparing the novel compounds; pharmaceutical formulations comprising a novel compound as active ingredient; and a method of treating ocular hypertension, glaucoma, hypertension of the cardiovascular system, acute and chronic congestive heart failure, and angina.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (A II) is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr. *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

There are several reports of non-peptidic angiotensin-II antagonists, most of which are nitrogen heterocycles substituted on a nitrogen with a substituted biphenylmethyl group. Some of the heterocycles reported are imidazoles (EP 253,310), imidazopyridines (EP 400,974), quinazolinones (EP 411,766), triazoles (EP 409,332), triazolinones (EP 412,594) pyrimidinones (EP 419,048) and pyrazoles (WO 91/15479).

In addition EP 443,983 and EP 490,820 describe A-II antagonists which omit the heterocycles and are acyl or alkoxycarbonyl derivatives of biphenylmethylamines.

DETAILED DESCRIPTION OF THE INVENTION

The novel compounds of this invention are represented by structural formula I:

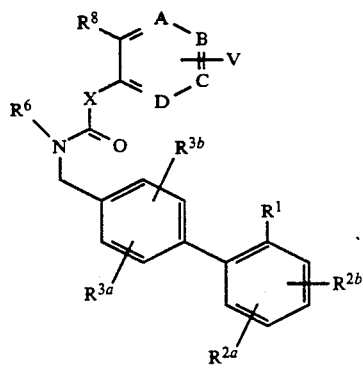

or a pharmaceutically acceptable salt thereof wherein:
A, B, C, and D are independently —CH= or —N=, with the proviso that at least two of them are —CH=;
X is —O— or —N(R$^7$)—;
R$^1$ is
 (a) —CO$_2$R$^4$,
 (b) —SO$_3$R$^5$,
 (c) —NHSO$_2$CF$_3$,
 (d) —PO(OR$^5$)$_2$,
 (e) —SO$_2$—NH—R$^9$,
 (f) —CONHOR$^5$,
 (g) —SO$_2$NH—heteroaryl,
 (h) —CH$_2$SO$_2$NH—heteroaryl,
 (i) —SO$_2$NHCOR$^{23}$,
 (j) —CH$_2$SO$_2$NHCOR$^{23}$,
 (k) —CONHSO$_2$R$^{23}$,
 (l) —CH$_2$CONHSO$_2$R$^{23}$,
 (m) —NHSO$_2$NHCOR$^{23}$,
 (n) —NHCONHSO$_2$R$^{23}$,
 (o) —SO$_2$NHSO$_2$R$^{23}$,
 (p) —SO$_2$NHCO$_2$R$^{20}$,
 (q) —SO$_2$NHCONHR$^{20}$, (r) 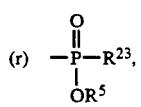

(s) 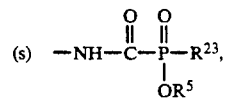

(t) 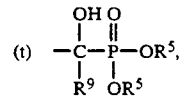

(u) 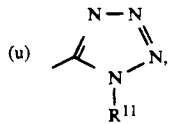

(v) —CH$_2$— 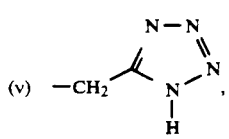

(w) —CONH— 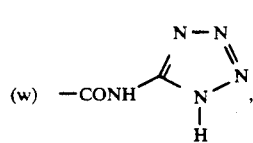

(x) —CONHNHSO$_2$CF$_3$, (y) 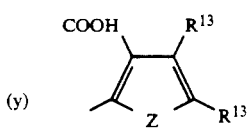

(z) 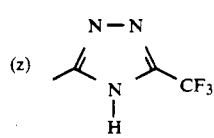

(aa) 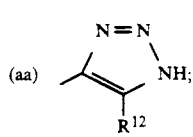

(bb) 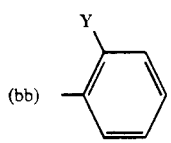

wherein:
Y is
  (1) —CO$_2$R$^4$,
  (2) —SO$_3$R$^5$,
  (3) —NHSO$_2$CF$_3$,
  (4) —PO(OR$^5$)$_2$, or
  (5) —SO$_2$—NH—R$^9$;
  (6) 1H-tetrazol-5-yl;
R$^{2a}$ and R$^{2b}$ are each independently:
  (a) hydrogen,
  (b) halo,
  (c) —NO$_2$,
  (d) —NH$_2$,
  (e) C$_1$-C$_4$-alkylamino,
  (f) —SO$_2$NHR$^9$,
  (g) —CF$_3$,
  (h) C$_1$-C$_4$-alkyl,
  (i) C$_1$-C$_4$-alkoxy; or
if R$^{2a}$ and R$^{2b}$ are on adjacent carbons, they can be bonded together to form a phenyl ring;
R$^{3a}$ is
(a) —H,
(b) halo,
(c) C$_1$-C$_6$-alkyl,
(d) C$_1$-C$_6$-alkoxy,
(e) C$_1$-C$_6$-alkoxy-C$_1$-C$_4$-alkyl;
R$^{3b}$ is
  (a) —H,
  (b) —halo,
  (c) —NO$_2$,
  (d) C$_1$-C$_6$-alkyl,
  (e) C$_1$-C$_5$-alkylcarbonyloxy,
  (f) C$_3$-C$_6$-cycloalkyl,
  (g) C$_1$-C$_6$-alkoxy,
  (h) —NHSO$_2$R$^4$,
  (i) hydroxy-C$_1$-C$_4$-alkyl,
  (j) aryl-C$_1$-C$_4$-alkyl,
  (k) C$_1$-C$_4$-alkylthio,
  (l) C$_1$-C$_4$-alkylsulfinyl,
  (m) C$_1$-C$_4$-alkylsulfonyl,
  (n) —NH$_2$,
  (o) C$_1$-C$_4$-alkylamino,
  (p) di(C$_1$-C$_4$-alkyl)amino,
  (q) —CF$_3$,
  (r) —SO$_2$—NHR$^9$,
  (s) aryl;
  (t) furyl; or
  when R$^{3a}$ and R$^{3b}$ are on adjacent carbons, they can be bonded together to form a phenyl ring;
R$^4$ is H, C$_1$-C$_6$-alkyl, —CH$_2$-aryl or aryl;
R$^5$ is H or —CH(R$^4$)—O—CO—R$^{4a}$ wherein R$^{4a}$ is C$_1$-C$_6$-alkyl, aryl or —CH$_2$-aryl;
R$^6$ is (a) C$_1$-C$_6$-alkyl, C$_2$-C$_6$-alkenyl or C$_2$-C$_6$-alkynyl each of which is unsubstituted or substituted with one or more substituents selected from the group consisting of aryl, C$_3$-C$_7$-cycloalkyl, halo, C$_1$-C$_4$-alkoxy, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and C$_1$-C$_4$-alkylthio,
  (b) C$_3$-C$_7$-cycloalkyl unsubstituted or substituted with one or more substituents selected from the group consisting of C$_1$-C$_4$-alkyl, C$_1$-C$_4$-alkoxy, C$_1$-C$_4$-alkylthio, OH, perfluoro-C$_1$-C$_4$-alkyl, and halo,
  (c) C$_3$-C$_7$-cycloalkyl-C$_1$-C$_3$-alkyl wherein the cycloalkyl is unsubstituted or substituted as in (b) above,
  (d) aryl, or
  (e) heteroaryl;
R$^7$ is (a) H,
  (b) phenyl unsubstituted or substituted with 1 or 2 substituents selected from the group consisting of halo, C$_1$-C$_4$-alkoxy, C$_1$-C$_4$-alkyl, —NO$_2$, —CF$_3$, —SO$_2$NR$^9$R$^{10}$, C$_1$-C$_4$-alkylthio, —OH, —NH$_2$, —COOR$^4$, C$_3$-C$_7$-cycloalkyl, and C$_3$-C$_{10}$-alkenyl,
  (c) C$_1$-C$_6$-alkyl, C$_2$-C$_6$-alkenyl or C$_2$-C$_6$-alkenyl each of which is unsubstituted or substituted with one or more substituents selected from the group consisting of aryl, heteroaryl, C$_3$-C$_7$-cycloalkyl, halo, C$_1$-C$_4$-alkoxy, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and C$_1$-C$_4$-alkylthio,
  (d) heteroaryl, or
  (e) C$_3$-C$_7$-cycloalkyl unsubstituted or substituted with one or more substituents selected from the group consisting of C$_1$-C$_4$-alkyl, C$_1$-C$_4$-alkoxy, C$_1$-C$_4$-alkylthio, —OH, —COOR$^4$, perfluoro-C$_1$-C$_4$-alkyl, and halo;
R$^8$ is —H, halo, —CF$_3$, —CH$_3$, —OCH$_3$ or —NO$_2$;
R$^7$ and R$^8$ may be joined together to form a ring with the atoms to which they are attached such that $R^7$-$R^8$ is (a) —Y—(CH$_2$)$_n$—Z, wherein n is 1 or 2; Y is a single bond, —C(O)— or —C(R$^{14}$)(R$^{15}$)—; Z is a single bond, —O—, —S(O)$_p$—, —N(R$^{16}$)—, —C(O)—, —CF$_2$— or —C(R$^{14}$)(R$^{15}$)—; and p is 0, 1 or 2, (b)

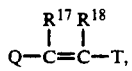

with the proviso that:
(1) Q is a single bond or —CO—;
(2) T is a single bond or —CO—; and
(3) at least one of Q and T is a single bond, (c)

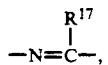

(d)

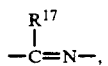

(e)

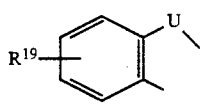

wherein U is —O—, —S—, —C(O)—, —CF$_2$— or —CH$_2$—, or (f)

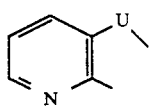

$R^9$ is H, C$_1$-C$_5$-alkyl, aryl or —CH$_2$-aryl;
$R^{10}$ is H, C$_1$-C$_4$-alkyl, or
$R^9$ and $R^{10}$ together can be —(CH$_2$)$_m$— where m is 3-6;
$R^{11}$ is H, C$_1$-C$_6$-alkyl, C$_2$-C$_4$-alkenyl, C$_1$-C$_4$-alkoxy-C$_1$-C$_4$-alkyl, or —CH$_2$—C$_6$H$_4$R$^{21}$;
$R^{12}$ is —CN, —NO$_2$ or —CO$_2$R$^4$;
$R^{13}$ is H, C$_2$-C$_4$-alkanoyl, C$_1$-C$_6$-alkyl, allyl, C$_3$-C$_6$-cycloalkyl, phenyl or benzyl;
$R^{14}$ and $R^{15}$ are independently H, C$_1$-C$_4$-alkyl, aryl, aryl-C$_1$-C$_2$-alkyl, C$_1$-C$_4$-alkoxycarbonyl, —CO$_2$H or —CH$_2$OH;
$R^{16}$ is (a) C$_1$-C$_6$-alkyl, either unsubstituted or substituted with C$_1$-C$_4$-alkoxy, C$_1$-C$_4$-alkyl-S(O)$_p$—, —CF$_3$, —OH, —CN, C$_1$-C$_4$-alkoxycarbonyl, —CO$_2$H, —CONR$^9$R$^{10}$ or —CO-aryl,
(b) C$_3$-C$_6$-alkenyl,
(c) C$_3$-C$_6$-cycloalkyl,
(d) aryl,
(e) heteroaryl,
(f) —COR$^{20}$,
(g) —CO$_2$R$^{20}$,
(h) —CONR$^9$R$^{10}$, or
(i) —SO$_2$R$^{20}$;

$R^{17}$ and $R^{18}$ are independently H, C$_1$-C$_4$-alkyl, aryl, aryl-C$_1$-C$_2$-alkyl, C$_1$-C$_4$-alkoxy, —CF$_3$, halo, C$_1$-C$_4$-alkoxycarbonyl, —CO$_2$H or —CH$_2$OH;
$R^{19}$ is C$_1$-C$_4$-alkyl, C$_1$-C$_4$-alkoxy, halo, —CF$_3$, C$_1$-C$_4$-alkyl-S(O)$_p$—, CF$_3$SO$_2$—, —CN, —NO$_2$, C$_1$-C$_4$-alkoxycarbonyl, —CO$_2$H, or —CH$_2$OH;
$R^{20}$ is C$_1$-C$_6$-alkyl, aryl or aryl-C$_1$-C$_2$-alkyl;
$R^{21}$ is H, —NO$_2$, —NH$_2$, —OH or —OCH$_3$;
$R^{23}$ is (a) phenyl, unsubstituted or substituted with one or two substituents selected from halo, —CH$_3$ and —CF$_3$, at least one or which occupies an ortho-position;
(b) heteroaryl, such as furan-2-yl, thiophen-2-yl, benzo[b]furan-2-yl, benzo[b]thiophene-2-yl, furan-3-yl, thiophen-3-yl, or oxazol-5-yl, unsubstituted or substituted with one or two substituents selected from halo, —CH$_3$ and CF$_3$ wherein at least one of the substituents is located adjacent to the carbonyl substituent and/or to a ring heteroatom;
(c) C$_3$-C$_6$-alkyl;
(d) C$_3$-C$_7$-cycloalkyl, unsubstituted or substituted at the 1- and/or 2-position with one to three substituents selected from halo, —CH$_3$ and —CH$_2$CH$_3$;
(e) C$_7$-C$_8$-bi- or tricycloalkyl;
(f) saturated 5- or 6-membered heterocyclyl linked through a carbon atom and containing one or two heteroatoms selected from oxygen and sulfur such as tetrahydrofuroyl, 1,3-dithiolane, or 1,3-dithiane.

$R^{24}$ is H, or R$^{25}$,
$R^{25}$ is (a) phenyl unsubstituted or substituted with 1 or 2 substituents selected from the group consisting of halo, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, —COOR$^4$, C$_3$-C$_7$-cycloalkyl, and C$_3$-C$_{10}$-alkenyl,
(b) C$_1$-C$_6$-alkyl, C$_2$-C$_6$-alkenyl or C$_2$-C$_6$-alkynyl each of which is unsubstituted or substituted with one or more substituents selected from the group consisting of aryl, C$_3$-C$_7$-cycloalkyl, halo, —OH, —O—C$_1$-C$_4$-alkyl, —NH$_2$, —NH(C$_1$-C$_4$-alkyl), —N(C$_1$-C$_4$-alkyl)$_2$, —NH—SO$_2$R$^4$, —COOR$^4$, —SO$_2$NHR$^9$, and —S—C$_1$-C$_4$-alkyl,
(c) an unsubstituted, monosubstituted or disubstituted aromatic 5 or 6 membered ring comprising one or two heteroatoms selected from the group consisting of N, O, and S, and wherein the substituents are members selected from the group consisting of —OH, —SH, C$_1$-C$_4$-alkyl, C$_1$-C$_4$-alkyloxy, —CF$_3$, —COOR$^4$, halo, and NO$_2$, or
(d) C$_3$-C$_7$-cycloalkyl unsubstituted or substituted with one or more substituents selected from the group consisting of C$_1$-C$_4$-alkyl, —O—C$_1$-C$_4$-alkyl, —S—C$_1$-C$_4$-alkyl, —OH, —COOR$^4$, perfluoro-C$_1$-C$_4$-alkyl, halo;

V is
(a) H,
(b) C$_1$-C$_5$-alkoxy,
(c) C$_1$-C$_5$-alkyl,
(d) hydroxy,
(e) C$_1$-C$_5$-alkyl-S(O)$_p$,
(f) —CN,
(g) —NO$_2$,
(h) —NR$^9$R$^{10}$, (i) $C_1$-$C_5$-alkyl-CONR$^9$R$^{10}$,
(j) —CONR$^9$R$^{10}$,
(k) —CO$_2$R$^9$,
(l) $C_1$-$C_5$-alkyl-carbonyl,
(m) CF$_3$,
(n) halogen,
(o) hydroxy-$C_1$-$C_4$-alkyl-,
(p) carboxy-$C_1$-$C_4$-alkyl-,
(q) —1H-tetrazol-5-yl,
(r) —NH—SO$_2$CF$_3$,
(s) aryl,
(t) $C_1$-$C_5$-alkyl-CO$_2$R$^9$,
(u) aryloxy,
(v) aryl-$C_1$-$C_3$-alkoxy,
(w) aryl-$C_1$-$C_3$-alkyl,
(x) carboxyphenyl,
(y) heteroaryl,
(z) 2-oxazolin-2-yl optionally bearing one or more $C_1$-$C_4$-alkyl substituents,
(aa) —(CH$_2$)$_t$OCOR$^{25}$,
(bb) —(CH$_2$)$_t$OCONR$^{24}$R$^{25}$,
(cc) —(CH$_2$)$_t$NR$^{24}$COR$^{25}$,
(dd) —(CH$_2$)$_t$NR$^{24}$CO$_2$R$^{25}$,
(ee) —(CH$_2$)$_t$NR$^{24}$CONR$^{24}$R$^{25}$,
(ff) —(CH$_2$)$_t$NR$^{24}$CON(CH$_2$CH$_2$)$_2$L,
(gg) —(CH$_2$)$_t$OCON(CH$_2$CH$_2$)$_2$L,
(hh) —N(CH$_2$CH$_2$)$_2$L,
(ii) —$C_1$-$C_5$-alkyl-CON(CH$_2$CH$_2$)$_2$L, or
(jj) —CON(CH$_2$CH$_2$)L;

t is 0, 1 or 2; and
L is a bond, —CH$_2$—, —O—, —S(O)$_p$— or —NR$^9$—.

The terms "alkyl", "alkenyl", "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The terms "halo" and halogen mean Cl, Br, I or F.

The term "aryl" is defined as phenyl or naphthyl, unsubstituted or substituted with one, two, or three substituents selected from the group consisting of $C_1$-$C_4$-alkyl, $C_1$-$C_4$-alkoxy, halo, CF$_3$, NO$_2$, $C_1$-$C_6$-alkyl-S(O)$_p$—, CF$_3$SO$_2$—, —OH, —NR$^9$R$^{10}$, —CO$_2$H, $C_1$-$C_4$-alkoxycarbonyl, —CONR$^9$R$^{10}$, —CN, NHCOR$^9$, and OCF$_3$.

The term "heteroaryl" is defined as a 5- or 6-membered aromatic ring consisting of carbon and from 1 to 3 heteroatoms selected from the group consisting of N, O, and S, such as pyridine, pyrimidine, pyrazine, triazine, furan, thiophene, oxazole, thiazole, imidazole, triazole, thiadiazole or the like, which may be fused to a benzo group and wherein the mono- or bicyclic system can be unsubstituted or substituted with one or two substituents selected from the group consisting of $C_1$-$C_4$-alkyl, $C_1$-$C_4$-alkoxy, $C_1$-$C_4$-alkylthio, —CF$_3$, halo, —NO$_2$, —CN, —OH, —NH$_2$, —NH($C_1$-$C_4$-alkyl), —N($C_1$-$C_4$-alkyl)$_2$, $C_1$-$C_4$-alkoxycarbonyl and —CO$_2$H.

One embodiment of the novel compounds is that represented by structural formula I, wherein X is —N(R$^7$)— wherein R$^7$ and R$^8$ are joined to form a ring such that R$^7$-R$^8$ is —Y—(CH$_2$)$_n$—Z—.

A class of compounds within this embodiment is that wherein Y is a single bond, C(R$^{14}$)(R$^{15}$) or CO; Z is a single bond; n=1 or 2; and
A, B, C and D are each —CH=;

R$^1$ is —SO$_2$NHCOR$^{23}$, —SO$_2$NHCO$_2$R$^{20}$, —SO$_2$NHCONHR$^{20}$ or 1H-tetrazol-5-yl;
R$^{2a}$, R$^{2b}$, R$^{3a}$ and R$^{3b}$ are independently H, $C_1$-$C_4$-alkyl, $C_1$-$C_4$-alkoxy or halo;
R$^6$ is $C_1$-$C_6$-alkyl, $C_2$-$C_6$-alkenyl, $C_2$-$C_6$-alkynyl, $C_3$-$C_7$-cycloalkyl, or $C_3$-$C_7$-cycloalkyl-$C_1$-$C_3$-alkyl; and
V is H, $C_1$-$C_5$-alkyl, $C_1$-$C_5$-alkoxy, —CF$_3$, -halo, —NO$_2$, —NR$^9$R$^{10}$, —NR$^{24}$COR$^{25}$, —NR$^{24}$CO$_2$R$^{25}$, —NR$^{24}$CONR$^{24}$R$^{25}$, —NR$^{24}$CON(CH$_2$CH$_2$)$_2$L, —CONR$^9$R$^{10}$, —CON(CH$_2$CH$_2$)$_2$L, or —CO($C_1$-$C_5$-alkyl);

Compounds representative of this class are:
1-[N-[[2'-[N-(2-chlorobenzoyl)sulfamoyl]biphenyl-4-yl]methyl]-N-pentylcarbamoyl]indoline;
1-[N-[[2'-[N-(2-chlorobenzoyl)sulfamoyl]biphenyl-4-yl]methyl]-N-pentylcarbamoyl]-1,2,3,4-tetrahydroquinoline;
1-[N-butyl-N-[[2'-[N-(2-chlorobenzoyl)sulfamoyl]-biphenyl-4-yl]methyl]carbamoyl]-1,2,3,4-tetrahydroquinoline;
1-[N-butyl-N-[[2'-[N-(2-chlorobenzoyl)sulfamoyl]-biphenyl-4-yl]methyl]carbamoyl]-3,4-dihydro-2(1H)quinolinone;
1-[N-[[2'-[N-(t-butoxycarbonyl)sulfamoyl]biphenyl-4-yl]methyl]-N-butylcarbamoyl]-1,2,3,4-tetrahydroquinoline;
1-[N-pentyl-N-[[2'-(1H-tetrazol-5-yl)biphenyl-4-yl]methyl]carbamoyl]-1,2,3,4-tetrahydroquinoline;
ethyl 1-[N-[[2'-[N-(2-chlorobenzoyl)sulfamoyl]biphenyl-4-yl]methyl]-N-pentylcarbamoyl]-1,2,3,4-tetrahydroquinoline-2-carboxylate;
1-[N-[[2'-[N-(2-chlorobenzoyl)sulfamoyl]biphenyl-4-yl]methyl]-N-pentylcarbamoyl]-7-nitro-1,2,3,4-tetrahydroquinoline;
7-amino-1-[N-[[2'-[N-(2-chlorobenzoyl)sulfamoyl]-biphenyl-4-yl]methyl]-N-pentylcarbamoyl]-1,2,3,4-tetrahydroquinoline;
7-(butyrylamino)-1-[N-[[2'-[N-(2-chlorobenzoyl)sulfamoyl]biphenyl-4-yl]methyl]-N-pentylcarbamoyl]-1,2,3,4-tetrahydroquinoline.

A second class of compounds within the class, wherein X is —N(R$^7$)— and R$^7$ and R$^8$ are joined to form a ring such that R$^7$-R$^8$ is —Y—(CH$_2$)$_n$—Z is that wherein Y is a single bond; Z is O, N(R$^{16}$), S, —CF$_2$—, —C(R$^{14}$)(R$^{15}$)— or —C(O)—; and n is 2;
A, B, C and D are each —CH=;
R$^1$ is —SO$_2$NHCOR$^{23}$, —SO$_2$NHCO$_2$R$^{20}$, —SO$_2$NHCONHR$^{20}$ or 1H-tetrazol-5-yl;
R$^{2a}$, R$^{2b}$, R$^{3a}$ and R$^{3b}$ are independently H, $C_1$-$C_4$-alkyl, $C_1$-$C_4$-alkoxy or halo;
R$^6$ is $C_1$-$C_6$-alkyl, $C_2$-$C_6$-alkenyl, $C_2$-$C_6$-alkynyl, $C_3$-$C_7$-cycloalkyl, or $C_3$-$C_7$-cycloalkyl-$C_1$-$C_3$-alkyl; and
V is H, $C_1$-$C_5$-alkyl, $C_1$-$C_5$-alkoxy, —CF$_3$, or halo.

Compounds representative of this class are:
1-[N-[[2'-[N-(2-chlorobenzoyl)sulfamoyl]biphenyl-4-yl]methyl]-N-pentylcarbamoyl]-3,4-dihydro-4(1H)-quinolinone;
4-[N-[[2'-[N-(2-chlorobenzoyl)sulfamoyl]biphenyl-4-yl]methyl]-N-pentylcarbamoyl]-3,4-dihydro-2H-1,4-benzothiazine;
4-[N-[[2'-[N-(2-chlorobenzoyl)sulfamoyl]biphenyl-4-yl]methyl]-N-pentylcarbamoyl]-3,4-dihydro-2H-1,4-benzoxazine;
1-acetyl-4-[N-[[2'-[N-(2-chlorobenzoyl)sulfamoyl]-biphenyl-4-yl]methyl]-N-pentylcarbamoyl]-1,2,3,4-tetrahydroquinoxaline;

1-[N-[[2'-[N-(2-chlorobenzoyl)sulfamoyl]biphenyl-4-yl]methyl]-N-pentylcarbamoyl]-4,4-difluoro-1,2,3,4-tetrahydroquinoline;

1-[N-[[2'-[N-(2-chlorobenzoyl)sulfamoyl]biphenyl-4-yl]methyl]-N-pentylcarbamoyl]-4-methyl-1,2,3,4-tetrahydroquinoline.

A third class of the embodiment wherein $R^7$ and $R^8$ are joined together is that wherein $R^7$-$R^8$ is

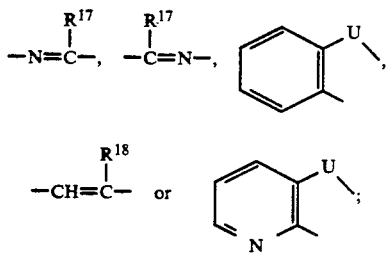

A, B, C and D are each —CH= or —N=;
$R^1$ is —SO$_2$NHCOR$^{23}$, —SO$_2$NHCO$_2$R$^{20}$, —SO$_2$NHCONHR$^{20}$ or 1H-tetrazol-5-yl;
$R^{2a}$, $R^{2b}$, $R^{3a}$ and $R^{3b}$ are independently H, C$_1$-C$_4$-alkyl, C$_1$-C$_4$-alkoxy or halo;
$R^6$ is C$_1$-C$_6$-alkyl, C$_2$-C$_6$-alkenyl, C$_2$-C$_6$-alkynyl, C$_3$-C$_7$-cycloalkyl, or C$_3$-C$_7$-cycloalkyl-C$_1$-C$_3$-alkyl; and
V is H, C$_1$-C$_5$-alkyl, C$_1$-C$_5$-alkoxy, —CF$_3$, or halo.

Compounds representative of this sub-class are:

10-[N-[[2'-[N-(2-chlorobenzoyl)sulfamoyl]biphenyl-4-yl]methyl]-N-pentylcarbamoyl]acridan;

10-[N-[[2'-[N-(2-chlorobenzoyl)sulfamoyl]biphenyl-4-yl]methyl]-N-pentylcarbamoyl]-9(10H)-acridone;

10-[N-[[2'-[N-(2-chlorobenzoyl)sulfamoyl]biphenyl-4-yl]methyl]-N-pentylcarbamoyl]phenoxazine;

3-chloro-1-[N-[[2'-[N-(2-chlorobenzoyl)sulfamoyl]biphenyl-4-yl]methyl]-N-pentylcarbamoyl]indazole;

1-[N-[[2'-[N-(2-chlorobenzoyl)sulfamoyl]biphenyl-4-yl]methyl]-N-pentylcarbamoyl]-3-methylindole;

1-[N-[[2'-[N-(2-chlorobenzoyl)sulfamoyl]biphenyl-4-yl]methyl]-N-pentylcarbamoyl]-2-methylbenzimidazole.

Another class of compounds within the embodiment wherein X is —N(R$^7$)— is that wherein R$^7$ is aryl, heteroaryl, aryl-C$_1$-C$_6$-alkyl, or C$_1$-C$_6$-alkyl.

A sub-class of compounds within this class is that wherein:

A, B, C and D are each —CH= or —N=;
$R^1$ is —SO$_2$NHCOR$^{23}$, —SO$_2$NHCO$_2$R$^{20}$, —SO$_2$NHCONHR$^{20}$ or —1H-tetrazol-5-yl;
$R^{2a}$, $R^{2b}$, $R^{3a}$, $R^{3b}$ are independently H, C$_1$-C$_4$-alkyl, C$_1$-C$_4$-alkoxy, or halo;
$R^6$ is C$_1$-C$_6$-alkyl, C$_2$-C$_6$-alkenyl, C$_2$-C$_6$-alkynyl, C$_3$-C$_7$-cycloalkyl; or C$_3$-C$_7$-cycloalkyl-C$_1$-C$_3$-alkyl;
$R^8$ is H, halo, or —CF$_3$
V is H, C$_1$-C$_5$-alkyl, C$_1$-C$_5$-alkoxy, CF$_3$, halo, —NO$_2$, —NR$^9$R$^{10}$, —NR$^{24}$COR$^{25}$, —NR$^{24}$CO$_2$R$^{25}$, —NR$^{24}$CONR$^{24}$R$^{25}$, —NR$^{24}$CON(CH$_2$CH$_2$)$_2$L, —CONR$^9$R$^{10}$, —CON(CH$_2$CH$_2$)$_2$L, or —CO(C$_1$-C$_5$-alkyl)

Compounds representative of this sub-class are:

1-butyl-1-[[2'-N-(2-chlorobenzoyl)sulfamoyl]biphenyl-4-yl]methyl]-3-phenyl-3-(2-pyridyl)urea.

1-[[2'-[N-(2-chlorobenzoyl)sulfamoyl]biphenyl-4-yl]methyl]-1-pentyl-3-phenyl-3-(2-pyridyl)urea;

1-benzyl-3-butyl-3-[[2'-[N-(2-chlorobenzoyl)sulfamoyl]biphenyl-4-yl]methyl]-1-phenylurea;

1-benzyl-3-[[2'-[N-(2-chlorobenzoyl)sulfamoyl]biphenyl-4-yl]methyl]-3-pentyl-1-phenylurea;

1-butyl-1-[[2'-[N-(2-chlorobenzoyl)sulfamoyl]biphenyl-4-yl]methyl]-3-methyl-3-[2-(trifluoromethyl)phenyl]urea;

1-methyl-3-pentyl-3-[[2'-(1H-tetrazol-5-yl)biphenyl-4-yl]methyl]-1-[2-(trifluoromethyl)phenyl]urea;

1-[[2'-[N-(2-chlorobenzoyl)sulfamoyl]biphenyl-4-yl]methyl]-3-methyl-1-pentyl-3-[2-(trifluoromethyl)phenyl]urea;

1-[[2'-[N-(2-chlorobenzoyl)sulfamoyl]biphenyl-4-yl]methyl]-3-methyl-1-pentyl-3-phenylurea;

1-[[2'-[N-(2-chlorobenzoyl)sulfamoyl]biphenyl-4-yl]methyl]-1-pentyl-3,3-diphenylurea;

1-[[2'-[N-(2-chlorobenzoyl)sulfamoyl]biphenyl-4-yl]methyl]-3-(3-chloro-2-pyridyl)-1-pentyl-3-phenylurea;

1-[[2'-[N-(2-chlorobenzoyl)sulfamoyl]biphenyl-4-yl]methyl]-3-(2-chlorophenyl)-1-pentyl-3-(2-pyridyl)urea;

1-benzyl-3-[[2'-[N-(2-chlorobenzoyl)sulfamoyl]biphenyl-4-yl]methyl]-3-pentyl-1-[2-(trifluoromethyl)phenyl]urea;

1-[[2'-[N-(2-chlorobenzoyl)sulfamoyl]biphenyl-4-yl]methyl]-3-[2-chloro-5-(valerylamino)phenyl]-3-methyl-1-pentylurea;

1-[[2'-[N-(2-chlorobenzoyl)sulfamoyl]biphenyl-4-yl]methyl]-3-(2-chlorophenyl)-3-methyl-1-pentylurea;

1-butyl-1-[[2'-[N-(2-chlorobenzoyl)sulfamoyl]-5'-propylbiphenyl-4-yl]methyl]-3-methyl-3-[2-(trifluoromethyl)phenyl]urea;

1-[[2'-[N-(2-chlorobenzoyl)sulfamoyl]-5'-ethylbiphenyl-4-yl]methyl]-3-[2-chloro-5-(propionylamino)phenyl]-3-methyl-1-pentylurea;

1-[[2'-[N-(t-butoxycarbonyl)sulfamoyl]biphenyl-4-yl]methyl]-1-butyl-3-[2-chloro-5-(valerylamino)phenyl]-3-methylurea;

1-[[2'-[N-(n-butoxycarbonyl)sulfamoyl]biphenyl-4-yl]methyl]-3-[2-chloro-5-(valerylamino)phenyl]-3-methyl-1-pentylurea;

1-[[2'-[N-(N-butylcarbamoyl)sulfamoyl]biphenyl-4-yl]methyl]-3-[2-chloro-5-(valerylamino)phenyl]-3-methyl-1-pentylurea;

1-[5-(N-butylcarbamoyl)-2-chlorophenyl]-3-[[2'-[N-(2-chlorobenzoyl)sulfamoyl]biphenyl-4-yl]methyl]-1-methyl-3-pentylurea;

1-[[2'-[N-(3-chloro-2-furoyl)sulfamoyl]biphenyl-4-yl]methyl]-3-methyl-1-pentyl-3-[2-(trifluoromethyl)phenyl]urea.

Another embodiment of the novel compounds of this invention is that represented by structure formula I, wherein X is —O—.

A class of compounds within this embodiment is that wherein
$R^1$ is —SO$_2$NHCOR$^{23}$, —SO$_2$NHCO$_2$R$^{20}$, —SO$_2$NHCONHR$^{20}$ or —1H-tetrazol-5-yl;
$R^{2a}$, $R^{2b}$, $R^{3a}$, $R^{3b}$ are independently H, C$_1$-C$_4$-alkyl, C$_1$-C$_4$-alkoxy, or halo;
$R^6$ is C$_1$-C$_6$-alkyl, C$_2$-C$_6$-alkenyl, C$_2$-C$_6$-alkynyl, C$_3$-C$_7$-cycloalkyl; or C$_3$-C$_7$-cycloalkyl-C$_1$-C$_3$-alkyl; and Compounds representative of this class are:

2-(trifluoromethyl)phenyl N-butyl-N-[[2'-[N-(2-chlorobenzoyl)sulfamoyl]biphenyl-4-yl]methyl]carbamate; and 2-(trifluoromethyl)phenyl N-[[2'-[N-(2-chlorobenzoyl)sulfamoyl]biphenyl-4-yl]methyl]-N-pentylcarbamate.

Another embodiment of the novel compounds of this invention is that wherein $R^6$ is heteroaryl and X is —O— or $NR^7$.

A class of compounds with this embodiment is that wherein $R^6$ is pyridyl or pyrimidyl.

Representative compounds within this class are the following:

1-[[2'-[N-(2-chlorobenzoyl)sulfamoyl]biphenyl-4-yl]methyl]-3-methyl-1-(2-methyl-4-pyridyl)-3-[2-(trifluoromethyl)phenyl]urea;

1-[[2'-[N-(2-chlorobenzoyl)sulfamoyl]biphenyl-4-yl]methyl]-3-methyl-1-(2,6-dimethyl-4-pyrimidyl)-3-[2-(trifluoromethyl)phenyl]urea;

1-(2-ethyl-4-pyridyl)-3-methyl-1-[[2'-(1H-tetrazol-5-yl)biphenyl-4-yl]methyl]-3-[2-(trifluoromethyl)phenyl]urea;

1-[[2'-[N-(2-chlorobenzoyl)sulfamoyl]-5'-ethylbiphenyl-4-yl]methyl]-3-[2-chloro-5-(propionylamino)phenyl]-3-methyl-1-(2-methyl-4-pyridyl)urea;

2-(trifluoromethyl)phenyl N-[[2'-[N-(2-chlorobenzoyl)sulfamoyl]biphenyl-4-yl]methyl]-N-(2-methyl-4-pyridyl)carbamate.

Abbreviations used in the reaction schemes and examples that follow are listed in Table I.

TABLE I

| Reagents | |
|---|---|
| Et$_3$N | triethylamine |
| iPr$_2$NEt | N,N-diisopropylethylamine |
| NBS | N-bromosuccinimide |
| AIBN | 2,2'-azobis(isobutyronitrile) |
| TFA | trifluoroacetic acid |
| CDI | 1,1'-carbonyldiimidazole |
| DBU | 1.8-diazabicyclo[5.4.0]undec-7-ene |
| (BzO)$_2$ | benzoyl peroxide |
| DCC | N,N'-dicyclohexylcarbodiimide |
| DMAP | 4-(dimethylamino)pyridine |
| Solvents | |
| DMF | dimethylformamide |
| DMSO | dimethylsulfoxide |
| THF | tetrahydrofuran |
| EtOH | ethanol |
| MeOH | methanol |
| AcOH | acetic acid |
| EtOAc | ethyl acetate |
| Others | |
| Me | methyl |
| Et | ethyl |
| iPr | isopropyl |
| t-Bu (Bu-t) | tert-butyl |
| Bu | n-butyl |
| Tr | trityl (triphenylmethyl) |
| Im | imidazol-1-yl |
| cat. | catalytic |
| TLC | thin layer chromatography |
| FAB-MS | fast atom bombardment mass spectrum |
| NMR | nuclear magnetic resonance (spectrum) |
| IR | infrared |
| UV | ultraviolet |
| HPLC | high pressure liquid chromatography |

DISCUSSION OF CHEMISTRY AND REACTION SCHEMES

The compounds of Formula I can be prepared by a variety of methods typified by those described below. Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and reaction time) should be chosen so that they are consistent with the nature of the functionality present in the molecule.

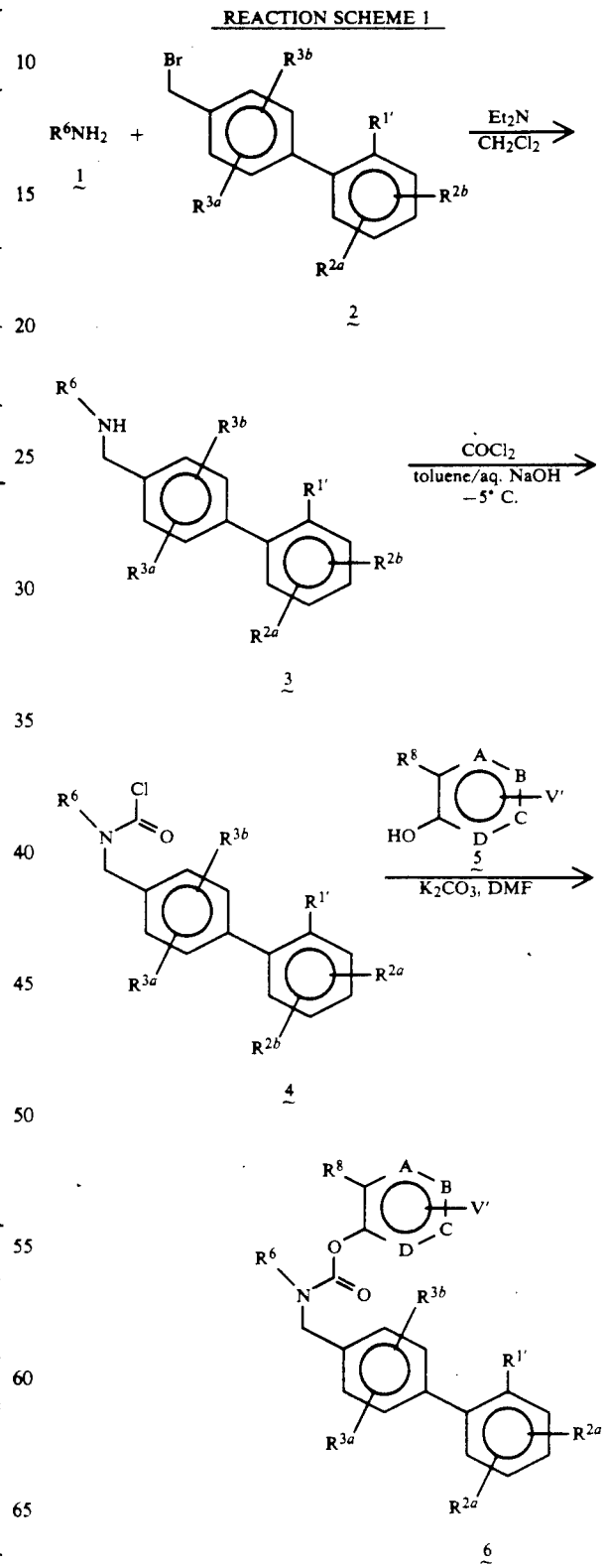

REACTION SCHEME 1

-continued
REACTION SCHEME 1

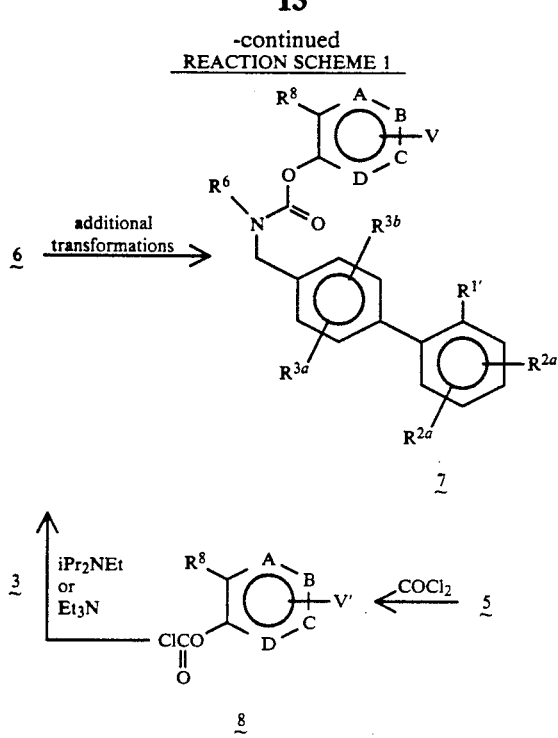

where V' is either V or a precursor of V and $R^{1'}$ is a precursor of $R^1$.

The synthesis of compounds of Formula I wherein X is O is outlined in Reaction Scheme I. Amine 1 (in particular, an aliphatic amine) is reacted with an appropriate biphenylmethyl bromide 2 in the presence of a base such as triethylamine, typically at room temperature, to give the secondary amine 3. This is readily converted to the carbamoyl chloride 4 by reaction with phosgene, typically in a well-stirred, two-phase system of toluene and aqueous sodium hydroxide at about $-5°$ C. In the presence of potassium carbonate in a solvent such as DMF, usually at about $80°$–$100°$ C., 4 reacts with a phenol (or aza analog thereof) 5 to yield the carbamate 6. Any further transformations, i.e., to provide the fully elaborated $R^1$ and V groups, can then be carried out to give the final product 7. In a variation, the phenolic compound 5 is treated with phosgene under standard conditions, yielding the chloroformate 8. Reaction of 8 with the secondary amine 3 in the presence of a base like N,N-diisopropylethylamine or triethylamine gives the carbamate 6.

REACTION SCHEME 2

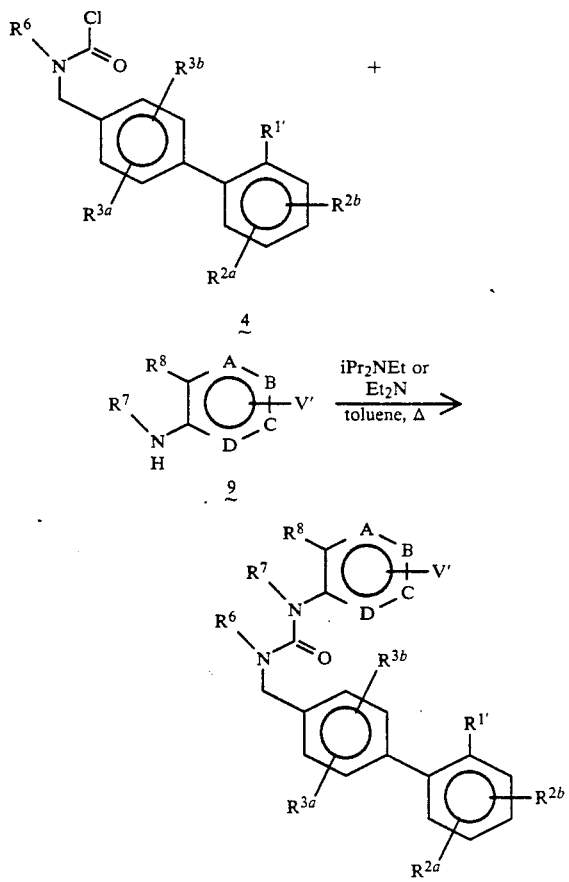

-continued
REACTION SCHEME 2

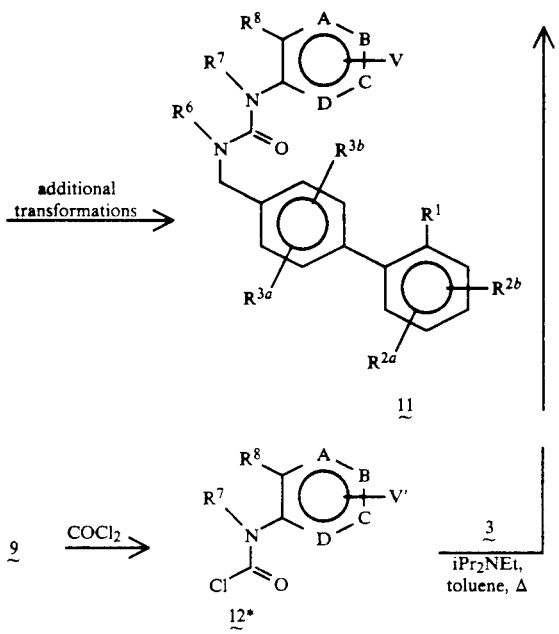

where V' is either V or a precursor of V and R¹' is a precursor of R¹.
*if R⁷ is H, this product is the isocyanate rather than the carbamoyl chloride Reaction Scheme 2 demonstrates the synthesis of compounds of Formula I wherein X is NR⁷. The carbamoyl chloride 4 (from Reaction Scheme 1) is reacted with the arylamine or heteroarylamine 9 in the presence of a base such as N,N-diisopropylethylamine or triethylamine, typically in toluene at about 90°-110° C., to yield the urea derivative 10. Similar urea syntheses using 2-butanone as solvent have been reported [W. E. Coyne and J. W. Cusic, *J. Med. Chem.*, 10, 541 (1967)]. As in Reaction Scheme 1, any further transformations of substituent groups can be carried out at this point to afford the fully elaborated products 11. In a variation of this route, particularly useful when 9 is less reactive owing to electronic and/or steric factors, the amine 9 is treated with phosgene in toluene, typically at room temperature or with heating up to about 90° C. if necessary, to give the carbamoyl chloride 12. This reaction may also be run in the presence of a base, for example triethylamine at about 5° C. [Coyne and Cusic, ibid]. Reaction of 12 with the secondary amine 3 (from Reaction Scheme 1) in the presence of a base such as N,N-diisopropylethylamine in a solvent such as toluene, typically at reflux, yields the urea 10. It should be noted that when R⁷ is H, the product obtained upon heating 9 with phosgene is not the carbamoyl chloride, but rather the corresponding isocyanate. The isocyanate can react similarly with 3 to give 10, and the synthesis of trisubstituted ureas by this method is well established [S. Ozaki and T. Nagoya, *Bull. Chem. Soc. Jpn.*, 30, 444 (1957)].

REACTION SCHEME 3

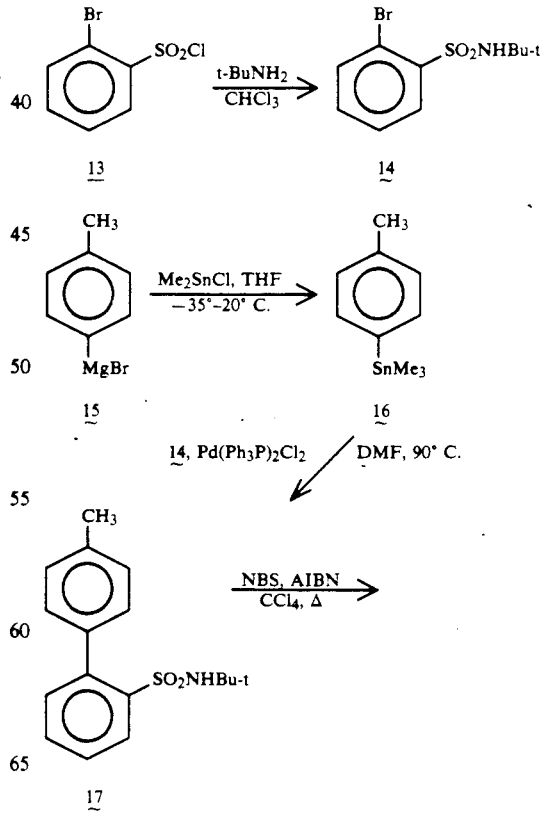

-continued
REACTION SCHEME 3

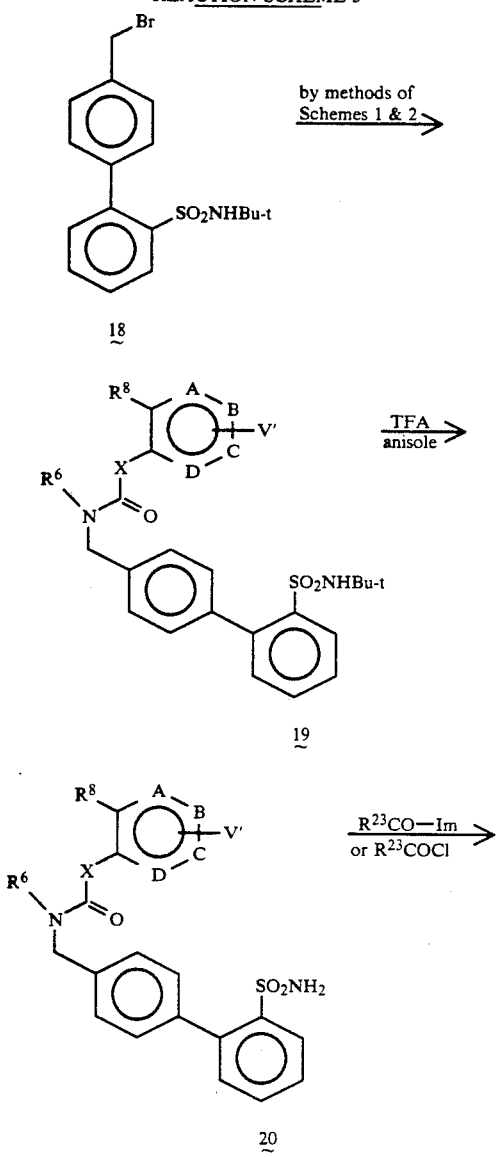

where V' is either V or a precursor of V.

Transformations demonstrating the assembly of the biphenylmethyl side chains and the elaboration of representative $R^1$ substituents are shown in Reaction Schemes 3–8. Thus, Reaction Scheme 3 illustrates the preparation of compounds of Formula I wherein $R^1$ is $-SO_2NHCOR^{23}$. Reaction of 2-bromobenzenesulfonyl chloride (13) with an excess of t-butylamine yields the t-butylsulfonamide 14. The trimethylstannyl derivative 16 may be prepared conveniently from p-tolylmagnesium bromide (15) by treatment with trimethyltin chloride at $-35°$ C. to room temperature. Cross-coupling of 16 with 14 catalyzed by bis(triphenylphosphine)palladium (II) chloride in DMF at about 90° C. affords the biphenyl derivative 17. The bromomethyl species 18 is obtained by heating 17 with N-bromosuccinimide (NBS) in carbon tetrachloride in the presence of an initiator such as 2,2'-azobis(isobutyronitrile)-(AIBN). The urea or carbamate 19 is elaborated by the methods of Reaction Schemes 1 and 2. The free sulfonamide 20 is obtained by deprotection of 19 with trifluoroacetic acid (TFA) in the presence of anisole. Conversion of 20 to the acylsulfonamide 21 is accomplished by reaction with an acylimidazolide (generated from the carboxylic acid in situ with 1,1'carbonyldiimidazole) in the presence of DBU in a solvent such as THF or with an acid chloride in pyridine (optionally in the presence of DMAP). Such methods have been described previously [J. T. Drummond and G. Johnson, *Tetrahedron Lett.*, 29, 1653(1988); R. Brans and R. J. W. Cremlyn, *J. Chem. Soc.* (C), 225 (1970)].

REACTION SCHEME 4

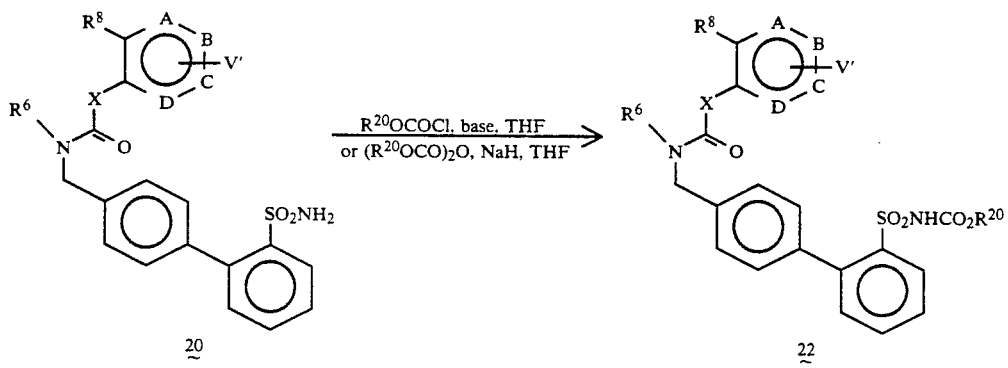

-continued
REACTION SCHEME 4

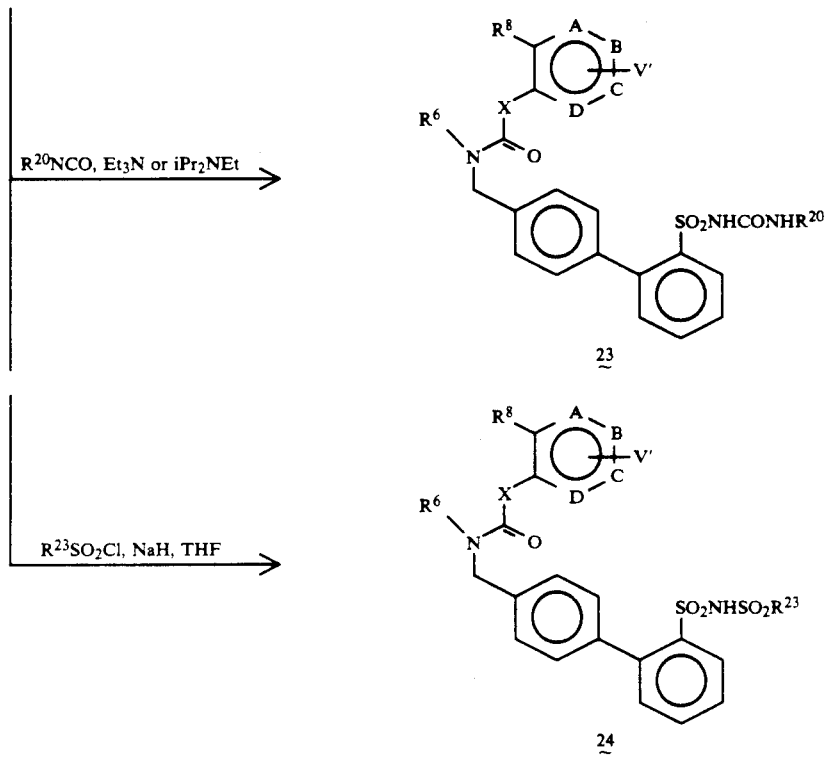

where V' is either V or a precursor of V.

Additional acidic sulfonamides at the $R^1$ position can be prepared as shown in Reaction Scheme 4. Treatment of the sulfonamide 20 (from Reaction Scheme 4) with a chloroformate, $R^{20}OCOCl$, in THF in the presence of an appropriate base (DBU, NaH, or pyridine/DMAP) affords the sulfonylcarbamate 22. For R=t-butyl, the reaction is preferentially carried out using di-t-butyl dicarbonate in the presence of sodium hydride. Reation of 20 with an isocyanate, $R^{20}NCO$, in the presence of a base such as triethylamine or N,N-diisopropyethylamine similarly provides the sulfonylurea 23 [G. F. Holland, D. A. Jaeger, R. L. Wagner, G. D. Laubach, W. M. McLamore, and S. Y. P'an, *J. Med. Pharm. Chem.*, 3, 99 (1961)]. Likewise, the disulfonimide 24 is obtained by treatment of 20 with a sulfonyl chloride, $R^{23}SO_2Cl$, in the presence of sodium hydride in THF.

REACTION SCHEME 5

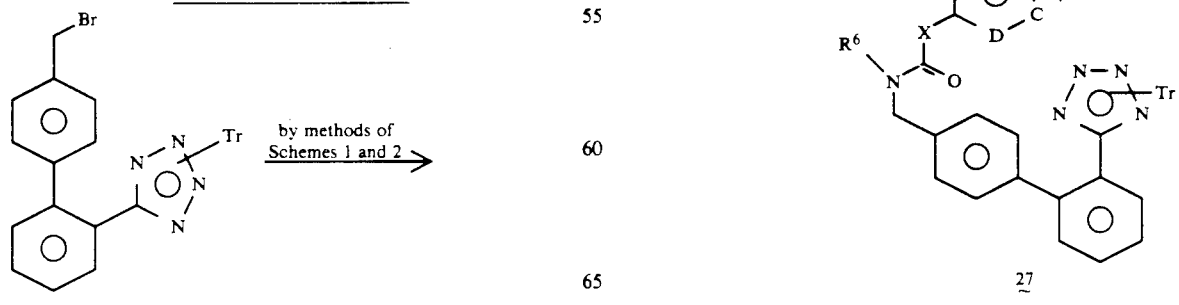

where V' is either V or a precursor of V.

For compounds of Formula I wherein $R^1$ is 1H-tetrazol-5-yl (Reaction Scheme 5), 5-[4'-(bromomethyl)-biphenyl-2-yl]-N-trityltetrazole (25) (prepared as in European Patent Application 291,969 or as modified in European Patent Application 400,835) is converted by the methods of Reaction Schemes 1 and 2 to the urea or carbamate 26. The trityl (triphenylmethyl) protecting group is removed by heating 26 in a mixture of acetic acid and water, usually at about 50°-60° C., to yield the tetrazole derivative 27.

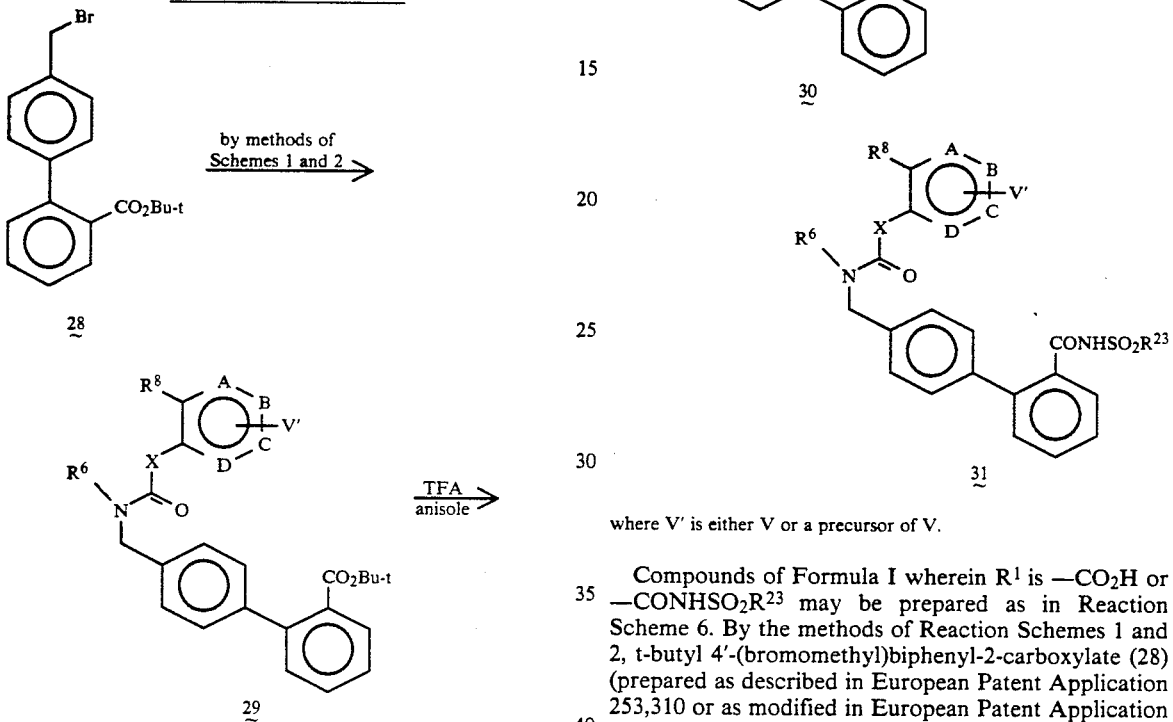

where V' is either V or a precursor of V.

Compounds of Formula I wherein $R^1$ is $-CO_2H$ or $-CONHSO_2R^{23}$ may be prepared as in Reaction Scheme 6. By the methods of Reaction Schemes 1 and 2, t-butyl 4'-(bromomethyl)biphenyl-2-carboxylate (28) (prepared as described in European Patent Application 253,310 or as modified in European Patent Application 400,835) is converted to the urea or carbamate 29. Treatment of this t-butyl ester with TFA in the presence of anisole affords the corresponding carboxylic acid 30, which may be further condensed with a sulfonamide, $R^{23}SO_2NH_2$, under conditions similar to those described in Reaction Scheme 3 to give an acylsulfonamide derivative of structure 31.

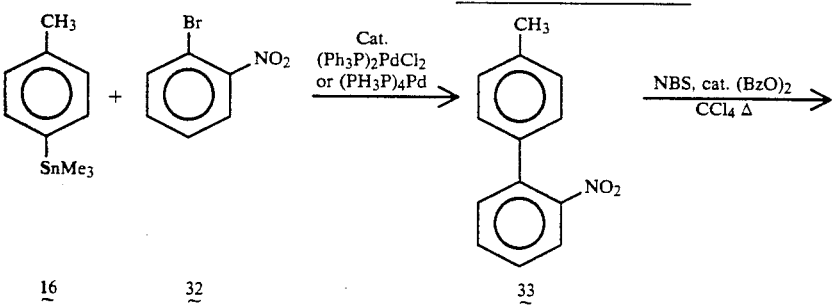

-continued
REACTION SCHEME 7

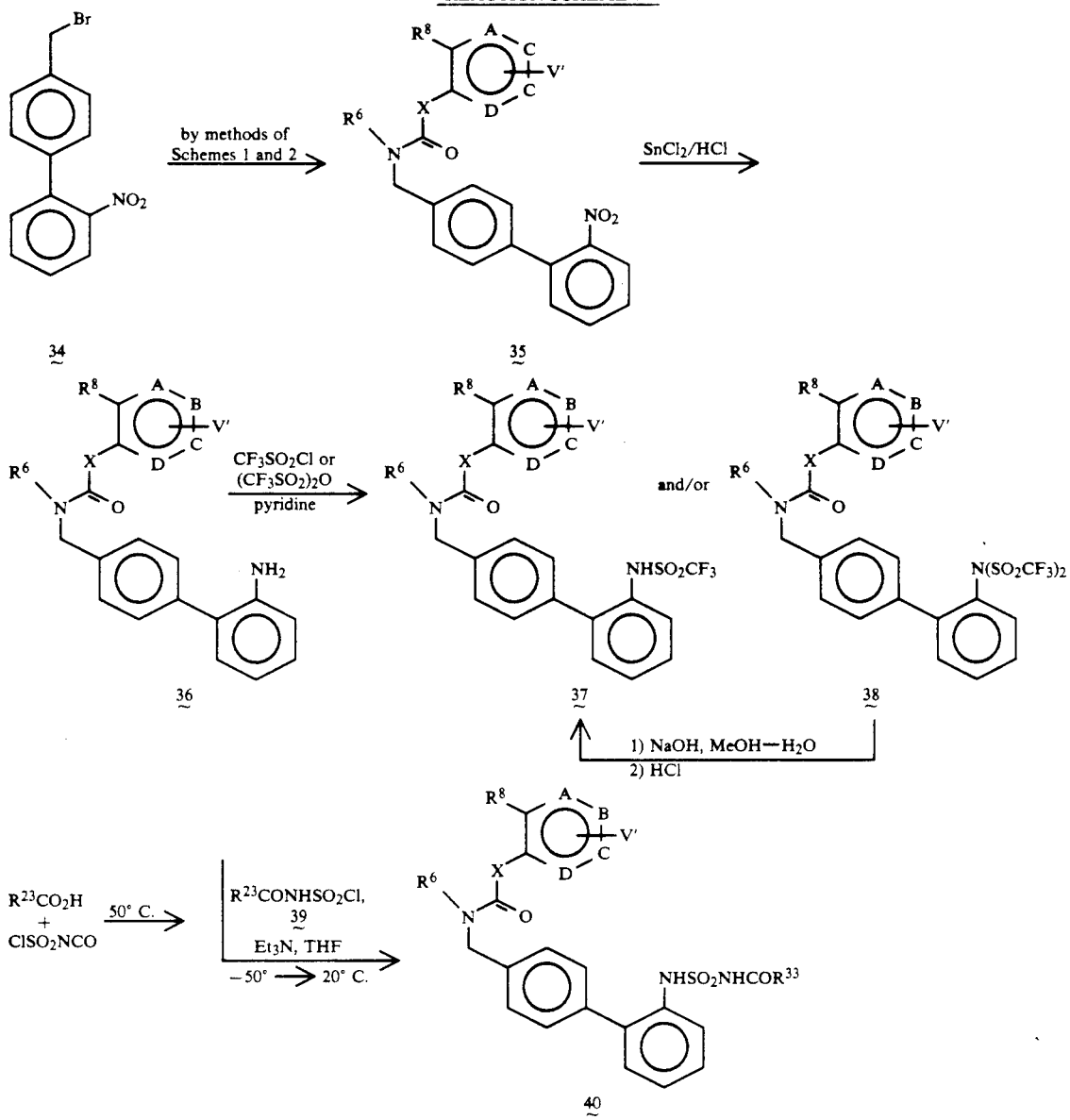

where V' is either V or a precursor of V.

Reaction Scheme 7 outlines the synthesis of compounds of Formula I wherein $R^1$ is triflamide (—NHSO$_2$CF$_3$) or acylsulfamide (—NHSO$_2$NHCOR$^{23}$). The trimethylstannane derivative 16 (from Reaction Scheme 3) is cross-coupled with o-bromonitrobenzene (32) in the presence of (Ph$_3$P)$_4$Pd or (Ph$_3$P)$_2$PdCl$_2$ catalyst to give the biphenyl derivative 33. Such couplings have been described by J. K. Stille, *Pure Appl. Chem.*, 57, 1771 (1985); T. R. Bailey, *Tetrahedron Lett.*, 27, 4407 (1986); and D. A. Widdowson and Y. -Z. Zheng, *Tetrahedron*, 42, 2111 (1986). Bromination of 33 with N-bromosuccinimide in the presence of catalytic benzoyl peroxide gives 34, which is converted to the urea or carbamate 35 by the methods of Reaction Schemes 1 and 2. Reduction of the nitro group of 35, preferably with stannous chloride/hydrochloric acid gives the amino derivative 36. Treatment of 36 with either trifluoromethanesulfonyl chloride or trifluoromethanesulfonic anhydride gives, depending on the conditions, either the mono(trifluoromethanesulfonyl) derivative 37 or the bis(trifluoromethanesulfonyl) derivative 38 as the major or exclusive product. The sulfonylation may be carried out in pyridine or, alternatively, in methylene chloride in the presence of a base such as 2,6-di-t-butyl-4-methylpyridine. The disulfonylated product 38 is converted to 37 by warming with sodium hydroxide in aqueous methanol. The amine 36 may also be treated with an acylsulfamoyl chloride 39 (prepared by reacting the carboxylic acid with chlorosulfonyl isocyanate at the 50° C.) in THF in the presence of triethylamine at −50° C. to room temperature, yielding the acylsulfamide 40.

REACTION SCHEME 8

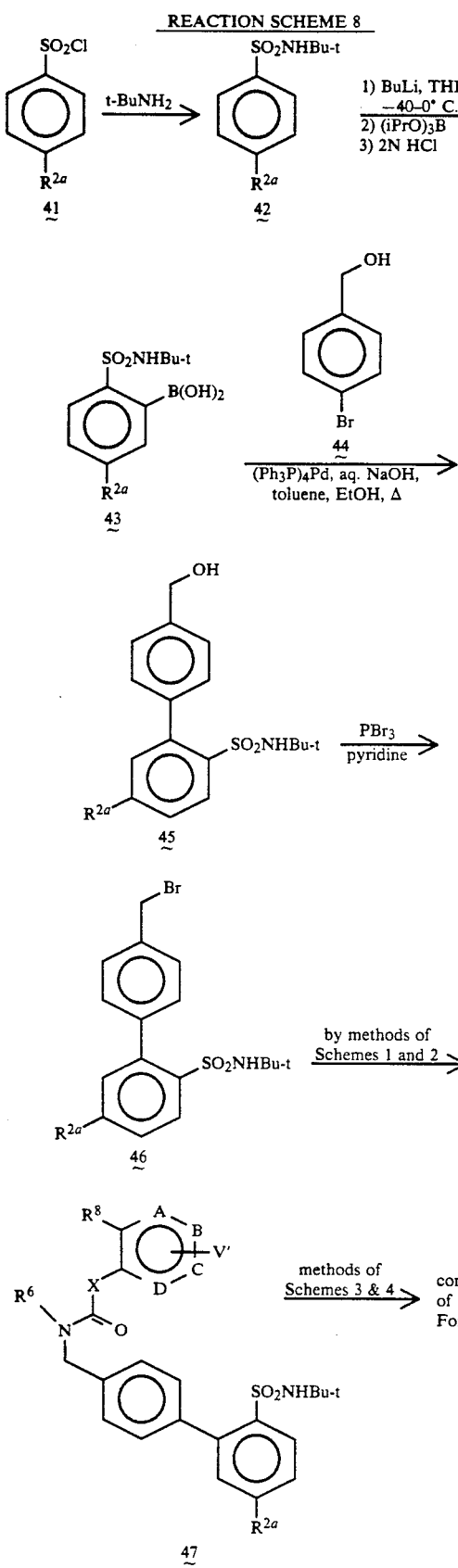

where V' is either V or a precursor of V.

The route shown in Reaction Scheme 8 is particularly useful for preparing analogs of 21, 22, 23 and 24 in which the distal ring of the biphenylmethyl side chain bears a substituent (for example, alkyl) at the 5'-position in addition to the sulfamoyl moiety at the 2'-position. A 4-substituted benzenesulfonyl chloride 41 is converted to the N-t-butylsulfonamide 42 as in Reaction Scheme 3. Based on a literature method [M. J. Sharp, W. Cheng, and V. Snieckus, *Tetrahedron Lett.*, 28, 5093(1987)], metalation ortho to the sulfonamide is achieved with n-butyllithium in THF at −40° to 0° C. Then treatment with triisopropyl borate followed by acidic work-up affords the boronic acid 43. This undergoes cross-coupling with 4-bromobenzyl alcohol (44) in the presence of tetrakis(triphenylphosphine)palladium(0) according to literature methods [M. J. Sharp, et al., op. cit.: N. Miyaura, T. Yanagi, and A. Suzuki, *Synth. Commun.*, 11, 513(1981)] to give the biphenylmethyl alcohol 45. Using standard conditions (for example, phosphorus tribromide in pyridine at about 0° C.), the alcohol 45 is converted to the bromo derivative 46. By the methods of Reaction Schemes 1 and 2, 46 is converted to the urea or carbamate derivative 47, which is further converted to compounds of Formula 1 using the methods of Reaction Schemes 3 and 4. Similar pathways can be used to prepare other analogs bearing $R^{2a}$, $R^{2b}$, $R^{3a}$, and/or $R^{3b}$ substitutents on the biphenyl moiety.

REACTION SCHEME 9

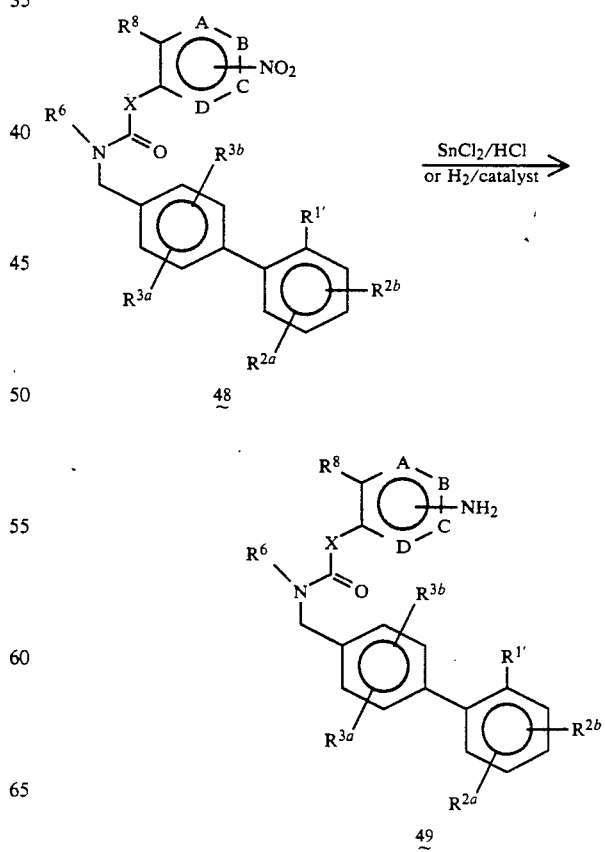

-continued
REACTION SCHEME 9

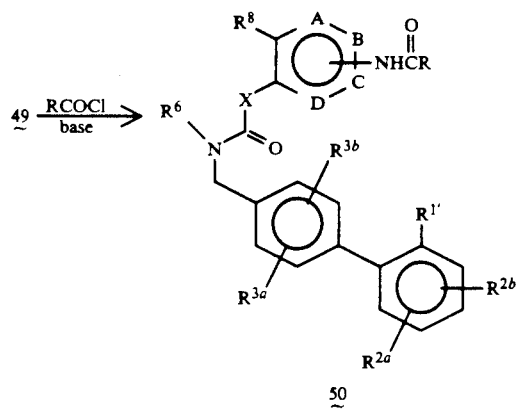

50

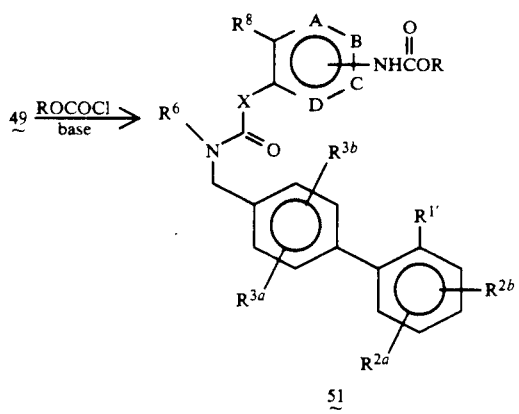

51

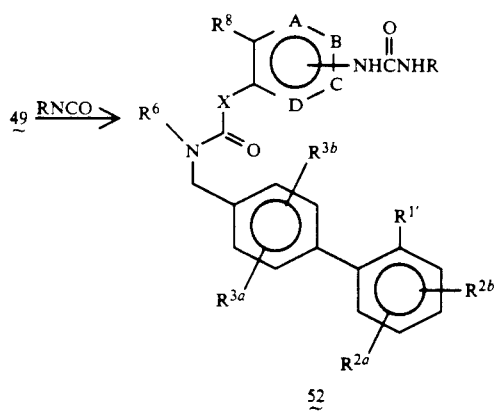

52

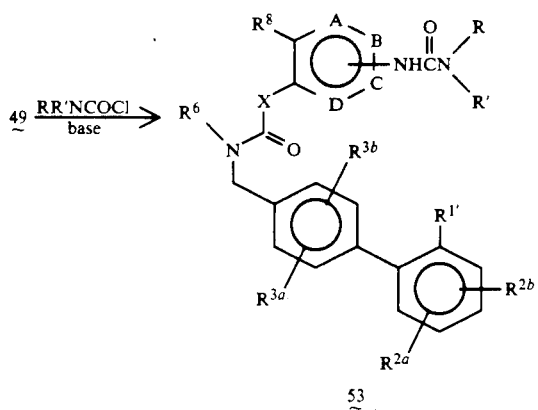

53

-continued
REACTION SCHEME 9

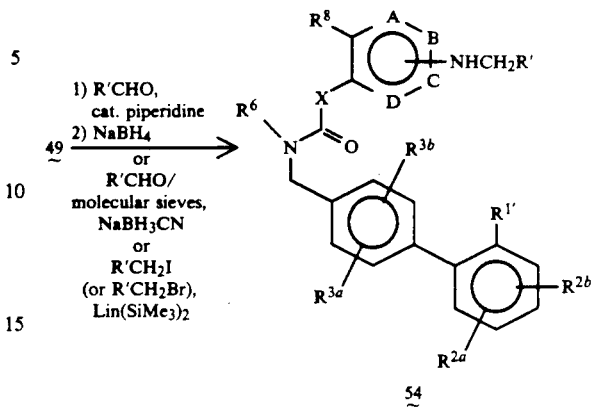

54

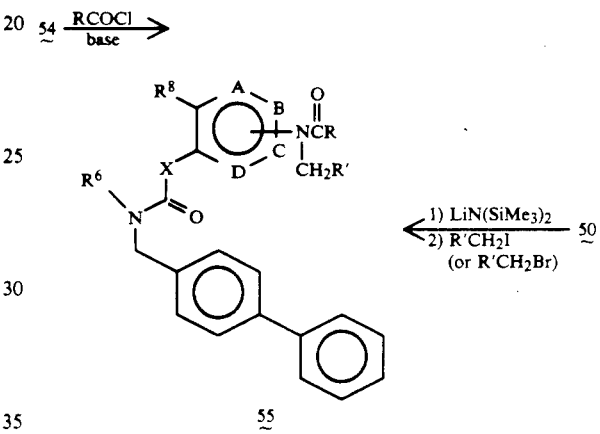

55 where $R^{1'}$ is either $R^1$ or a precursor of $R^1$.

After synthesis of the carbamate (6) or urea (10) derivative according to Reaction Schemes 1 and 2 and any other relevant schemes, various functional group transformations may be carried out in order to elaborate the desired V substituent. In many cases, such transformations may be accomplished either at a stage where the $R^1$ substituent is in its final form or at a precursor or protected stage. When the transformations are carried out at a precursor stage (for example, the t-butylsulfonamide precursor to 21–24), conversion to the final $R^1$ substituent is accomplished as indicated in the appropriate Reaction Schemes. Whether there is a preference for carrying out the transformations at one stage or another depends on the particular reaction conditions and will be apparent to one skilled in the art. At the time the urea or carbamate is assembled according to the previous schemes, the V substituent may be present in precursor form (for example, $NO_2$ or $CO_2$-alkyl).

Reaction Schemes 9 and 10 illustrate the elaboration of a number of the V substituents. As shown in Reaction Scheme 9, intermediate 48, which contains a nitro substituent and is prepared according to the previous schemes, is reduced, as appropriate, with stannous chloride in the presence of concentrated hydrochloric acid or by catalytic hydrogenation to give the amino derivative 49. In the presence of a base such as sodium hydride, 49 can be reacted with an acid chloride to give the amide 50, with a chloroformate to give the carbamate 51, with an isocyanate to give the amide 52, or with a carbamoyl chloride to give a trisubstituted urea 53. Also, 49 can be converted to a substituted-amino derivative 54. For R'=aryl, this may be accomplished conveniently by first heating 49 with the aldehyde in the presence of a catalytic amount of piperidine in a solvent such as isopropanol. The intermediate Schiff base is then reduced (optionally without isolation) by use of sodium borohydride in ethanol to provide 54. For R'=alkyl or aralkyl, the transformation may be accomplished by reacting 49 with the aldehyde in the presence of molecular sieves and sodium cyanoborohydride (present initially or added later), preferably at about 10°–40° C. Alternatively, for R'=aryl, alkyl, hydrogen, etc., 49 may be deprotonated with a strong base such as lithium bis(trimethylsilyl)amide in a solvent such as DMF and then reacted with the appropriate alkyl or aralkyl iodide or bromide to afford 54. Subsequently, 54 can be acylated as described above to yield the tertiary amide 55, which may also be prepared by alkylation of 50 in the presence of a strong base such as lithium bis(trimethylsilyl)amide in a solvent such as DMF.

-continued

Reaction Scheme 10

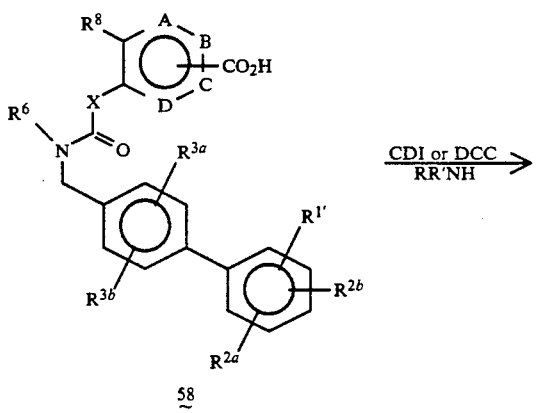

Reaction Scheme 10

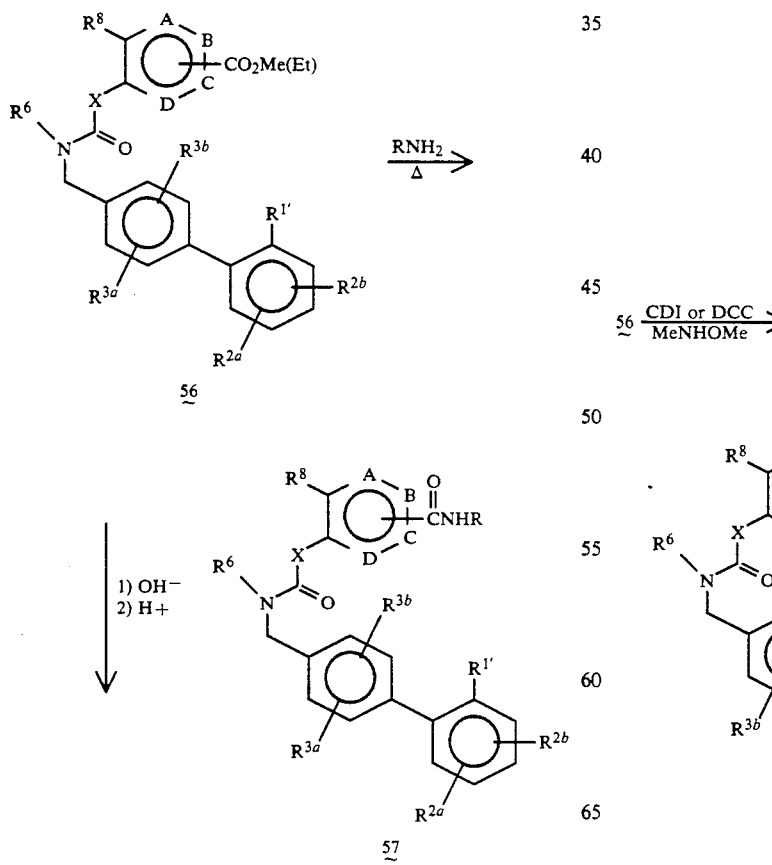

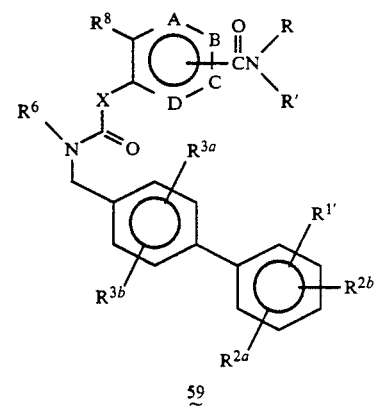

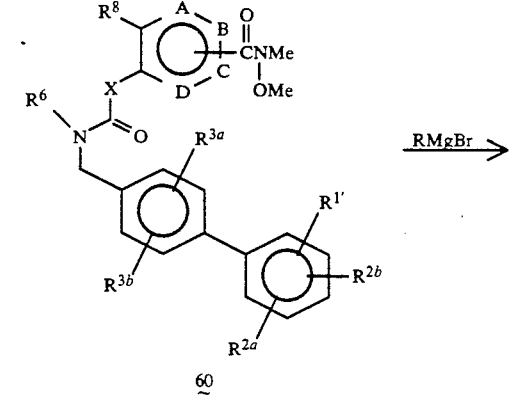

-continued
Reaction Scheme 10

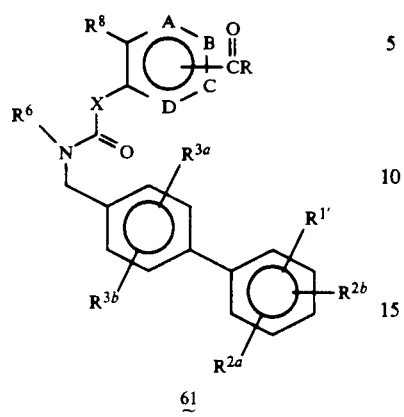

61 where R[1'] is either R[1] or a precursor of R[1].

In Reaction Scheme 10, intermediate 56, which bears a methyl or ethyl ester substituent and is synthesized according to the previous reaction schemes, is treated with a neat amine, generally at about 20°–100° C., to provide the amide 57. This method is particularly useful for primary amines. Compound 56 may also be saponified under standard conditions to the carboxylic acid 58. With use of a condensing agent such as 1,1'-carbonyldiimidazole or N,N'-dicyclohexylcarbodiimide, 58 can be reacted with an amine to give the amide product 59. This method is suitable for secondary as well as primary amines. Similarly, 56 is converted to the N-methoxy-N-methylamide 60. Following the Weinreb method [S. Nahm and S. M. Weinreb, *Tetrahedron Lett.*, 22, 3815(1981)], 60 can be reacted with an alkylmagnesium halide to afford the ketone product 61.

REACTION SCHEME 11

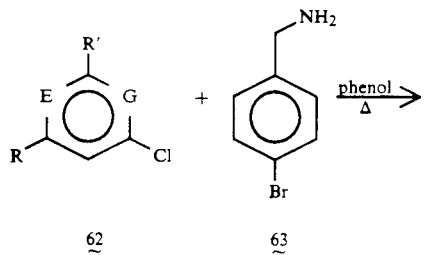

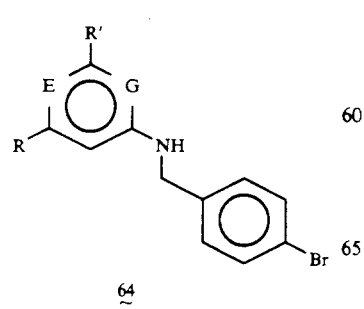

-continued
REACTION SCHEME 11

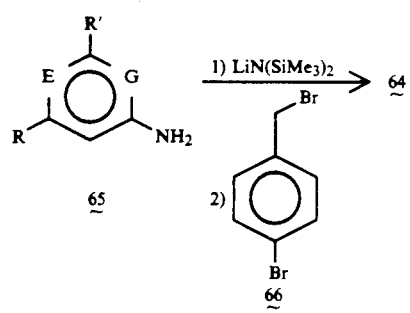

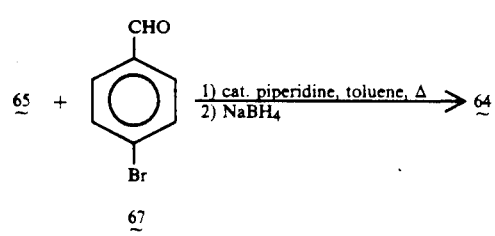

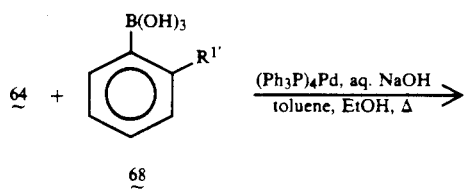

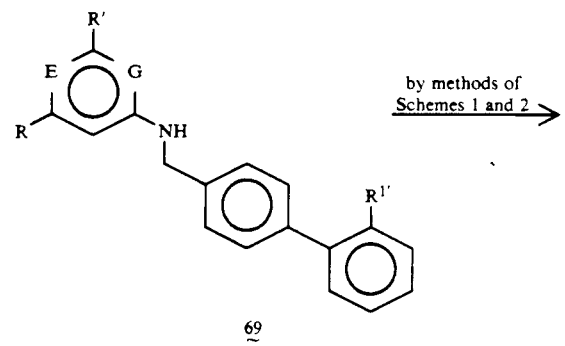

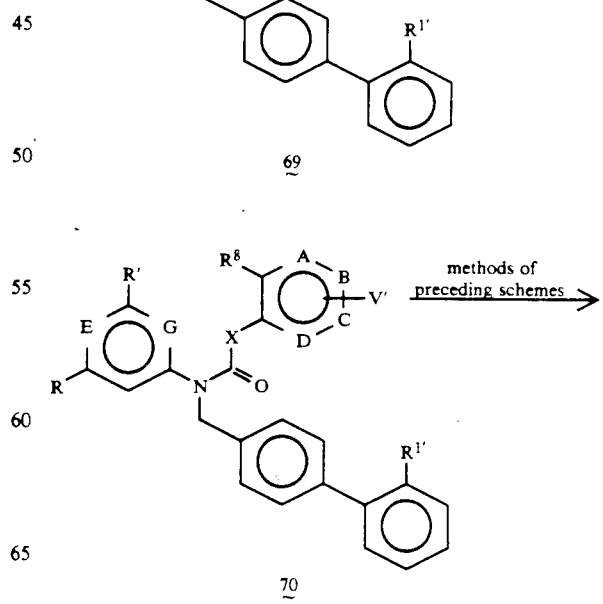

-continued
REACTION SCHEME 11

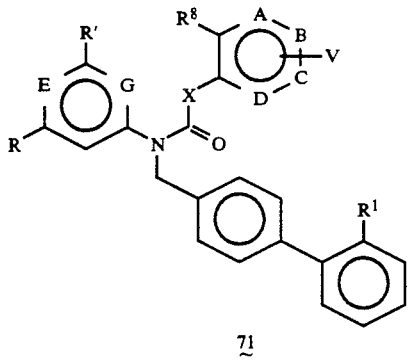

71 where E and G are independently N or CR", with the proviso that at least one of E and G is N;

R, R', and R" are H, alkyl, etc.;

$R^{1'}$ is a protected precursor of $R^1$; and

V' is either V or a precursor of V.

The preparation of compounds of Formula I wherein $R^6$ is heteroaryl (for example, substituted 4-pyridyl or 4-pyrimidyl) is shown in Reaction Scheme 11. The heteroaryl compound 62, which contains a displaceable chloro group, is reacted with 4-bromobenzylamine (63) in phenol, typically at about 100°–175° C. [D. M. Hall and E. E. Turner, *J. Chem. Soc.*, 694(1945)], to give the substituted-amino heterocycle 64. Alternatively, aminoheterocycle 65 can be deprotonated with a strong base such as lithium bis(trimethylsilyl)amide in a solvent such as THF or DMF followed by treatment with 4-bromobenzyl bromide (66) to yield 64 [for analogous reaction: R. G. Jacomb and W. O. Kermack, *J. Chem. Soc.*, 62 (1946)]. Still another route to 64 is by condensation of 65 with 4-bromobenzaldehyde (67), typically by heating in toluene at reflux in the presence of catalytic piperidine under a Dean-Stark trap [J. Renault, J.-C. Cartron, and J. Berlot, *Bull. Soc. Chim. Fr.*, 2123 (1968)], and reduction of the intermediate Schiff base with sodium borohydride in ethanol. (It should be noted that the last two methods are also applicable for the synthesis of compounds of Formula I wherein $R^6$ is aryl.) Palladium(0)-catalyzed cross-coupling of 64 with an appropriate ortho-substituted phenylboronic acid 68 (prepared as in Reaction Scheme 8) affords the biphenyl derivative 69. By the methods of Reaction Schemes 1 and 2, 69 is converted to the urea or carbamate 70, which is further elaborated to the final product 71 by the previously described methods.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine salts, salts with amino acids like arginine, lysine, and the like. Also, salts with organic and inorganic acids may be prepared; e.g., HCl, HBr, $H_2SO_4$, $H_3PO_4$, methanesulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following three ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}I$-Sar$^1$Ile$^8$-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethanesulfonyl fluoride (PMSF)(0.1 MM)]. (For screening of compounds, generally duplicates of tubes are used). To the membrane preparation (0.5 ml) there was added $^3H$-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3H$-angiotensin II was presented as a measure of the efficacy of such compounds as AII antagonists.

Receptor assay using rat brain membrane preparation

Membranes from rat brain (thalamus, hypothamus and midbrain) were prepared by homogenization in 50 mM Tris HCl (pH 7.4), and centrifuged at 50,000×g. The resulting pellets were washed twice in 100 mM NaCl, 5 mM Na$_2$•EDTA, 10 mM Na$_2$HPO$_4$ (pH 7.4) and 0.1 mM PMSF by resuspension and centrifugation. For binding assays, the pellets were resuspended in 160 volumes of binding assay buffer (100 mM NaCl, 10 mM Na$_2$HPO$_4$, 5 mM Na$_2$•EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I-Sar$^2$Ile$^8$ or [$^{125}$I]Sar$^1$, Ile$^8$-angiotensin II binding assays, 10 µl of solvent (for total binding), Sar$^1$, Ile$^8$-angiotensin II (1 µM) (for nonspecific binding) or test compounds (for displacement) and 10 µl of [$^{125}$I]Sar$^1$, Ile$^8$-angiotensin II (23–46 pM) were added to duplicate tubes. The receptor membrane preparation (500 µl) was added to each tube to initiate the binding reaction. The reaction mixtures were incubated at 37° C. for 90 minutes. The reaction was then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters was counted using a gamma counter.

Using the methodology described above, representative compounds of the invention were evaluated and all were found to exhibit an activity of IC$_{50}$<10 µM against the AT$_1$ and AT$_2$ subtype receptors thereby demonstrating and confirming the utility of the compounds of the invention as effective A II antagonists with "balanced" AT$_1$/AT$_2$ activity.

The antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate-60 strokes per minute, volumn-1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later antagonists of the Formula I were administered intravenously or orally. Angiotensin II was then typically given at 5, 10, 15, 30, 45 and 60 minute intervals and every half hour thereafter for as long as the test compound showed activity. The change in the mean arterial blood pressure was recorded for each angiotensin II challenge and the percent inhibition of the angiotensin II response was calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, protein-uria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidine sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propanolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

2-(Trifluoromethyl)phenyl N-Butyl-N-[[2′-[N-(2-chlorbenzoyl)sulfamoyl]biphenyl-4-yl]methyl]carbamate Step A: 2-Bromo-N-(tert-butyl)benzenesulfonamide To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 hours, then the mixture evaporated to dryness. Flash chromatography (silica gel, 15% ethyl acetate-hexane) afforded the title compound (2.12 g, 84%) as a white solid; $^1$H NMR (300 MHz, CDCl$_3$) δ8.18 (d, J=8.5 Hz, 1H), 7.73 (d, J=8.5 Hz, 1H), 7.50–7.35 (m, 2H), 5.11 (s, 1H), 1.20 (s, 9H).

Step B: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 hours; then saturated ammonium chloride solution (10 ml) was added, followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (bp 39°–40° C., 0.1 mm Hg) which was further purified by flash chromatography (silica gel, hexane) to give p-tolyltrimethyltin (7.30 g, 82%) as a colorless liquid; $^1$H NMR (300 MHz, CDCl$_3$) δ7.40 (d, J=7.7 Hz, 2H), 7.19 (d, J=7.7 Hz, 2H), 2.34 (s, 3H), 0.30 (s, 9H).

Step C: 2′-(N-t-Butylsulfamoyl)-4-methylbiphenyl

2-Bromo-N-(tert-butyl)benzenesulfonamide (from Step A) (1.00 g, 3.92 mmol), p-tolyltrimethyltin (from Step B) (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 hours. The black suspension was cooled to room temperature, then filtered through a pad of Celite which was washed with tetrahydrofuran. The colorless filtrate was evaporated to dryness then chromatographed (silica gel, 10% ethyl acetate-hexane) to give the title compound (0.88 g, 74%) as a white solid; $^1$H NMR (300 MHz, CDCl$_3$) δ8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step D: [2′-(N-t-Butylsulfamoyl)biphenyl-4-yl]-methyl bromide

N-Bromosuccinimide (387 mg, 2.17 mmol), α,α′-azobis(isobutyronitrile) (catalytic), 2′-(N-t-butylsulfamoyl)-4-methylbiphenyl (from Step C) (550 mg, 1.81 mmol) and carbon tetrachloride (50 ml) were heated with stirring at reflux for 3 hours. After cooling to room temperature the mixture was filtered and the filtrate evaporated to dryness. Flash chromatography (silica gel, initially 10 and then 20% ethyl acetate-hexane) afforded the title compound [699 mg, 77% pure (the remainder of the material was the corresponding dibromo derivative)] as a white solid; $^1$H NMR (300 MHz, CDCl$_3$) $\delta$8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

Step E:
N-Butyl-N-[[2'-(N-t-butylsulfamoyl)biphenyl-4-yl]methyl]amine

To a solution of 3.9 mL (2.9 g, 39.5 mmole) of n-butylamine and 1.3 mL (0.95 g, 9.4 mmole) of triethylamine in 40 mL of dry methylene chloride was added 3.39 g (7.9 mmole, based on 89% purity) of [2'-(N-t-butylsulfamoyl)biphenyl-4-yl]methyl bromide (prepared as in Step D). The mixture was stirred under N$_2$ at room temperature overnight and then concentrated to dryness. The viscous oil was dissolved in some fresh methylene chloride and evaporated onto silica gel (the minimum amount required to give a dry powder). This was layered on top of a silica gel flash column, which was eluted initially with 1:1 hexane-EtOAc and then with a larger volume of EtOAc alone. The fractions containing pure product were combined and concentrated in vacuo to yield 2.1 g (70%) of the title compound as a white solid, mp 98°–99° C., homogeneous by TLC (EtOAc); FAB-MS m/e 375 (M+1)$^+$.

400 MHz NMR (CDCl$_3$) $\delta$0.90 (t, J=7.3 Hz, 3H), 0.97 (s, 9H), 1.35 (m, 2H), 1.54 (m, 2H), 2.65 (t, J=7.3 Hz, 2H), 3.63 (br s, 1H), 3.87 (2, 2H), 7.25–7.6 (m, 7H), 8.14 (d, J=8 Hz,1H).

Analysis: C$_{21}$H$_{30}$N$_2$O$_2$S•0.25H$_2$O), Calcd: C, 66.54; H, 8.11; N, 7.39. Found: C, 66.91; H, 8.31; N, 7.27.

Step F:
N-Butyl-N-[[2'-(N-t-butylsulfamoyl)biphenyl-4-yl]methyl]carbamoyl chloride A solution of 1.8 g (4.81 mmole) of N-butyl-N-[[2'-(N-t-butylsulfamoyl)biphenyl-4-yl]methyl]amine (from Step E) in 35 mL of toluene was cooled to −5° C. and treated with 9.6 mL (24 mmole) of 2.5M sodium hydroxide (aqueous), followed by 7.5 mL (14.5 mmole) of phosgene in toluene. The cold mixture was stirred for 45 minutes and then filtered to remove a white precipitate. The layers of the filtrate were separated, and the toluene phase was concentrated in vacuo to yield 1.21 g (58%) of the title compound as a white solid, mp 128°–129° C.; homogeneous by TLC (3:1 hexane-EtOAc); IR spectrum $\nu_{CO}$1745 cm$^{-1}$; FAB-MS m/e 438 (M+1)$^+$. The $^1$H NMR spectrum indicated the presence of two rotameric forms.

400 MHz NMR (CDCl$_3$) $\delta$0.93 (m, 3H), 0.97 (s, 9H), 1.33 (m, 2H), 1.61 (m, 2H), 3.39 (m, 2H), 3.47 (s, 1H), 4.61 4.74 (s, total 2H), 7.25–7.6 (m, 7H), 8.15 (d, J=7.5 Hz, 1H).

Analysis: (C$_{22}$H$_{29}$ClN$_2$O$_3$S), Calcd: C, 60.47; H, 6.69; N, 6.41. Found: C, 60.41; H, 6.93; N, 6.29.

Step G:
2-(Trifluoromethyl)phenyl N-Butyl-N-[[2'-(N-t-butylsulfamoyl)biphenyl-4-yl]methyl]carbamate A mixture of 171 mg (0.391 mmole) of N-butyl-N-[[2'-(N-t-butylsulfamoyl)biphenyl-4-yl]methyl]carbamoyl chloride (from Step F), 63.9 mg (0.394 mmole) of $\alpha,\alpha,\alpha$-trifluoro-o-cresol, 66 mg (0.48 mmole) of anhydrous potassium carbonate, and 3 mL of DMF was stirred under N$_2$ at 90° C. overnight. The cooled mixture was partitioned between 20 mL of 2N HCl and 20 mL of EtOAc. The organic layer was washed with H$_2$O (2×30 mL), dried over sodium sulfate, filtered, and concentrated in vacuo. The residual oil was flash chromatographed on silica gel (gradient elution with 20–35% EtOAc in hexane to yield 37.4 mg (17%) of the title compound as a yellow oil, homogeneous by TLC in 3:1 hexane-EtOAc; FAB-MS m/e 562 (M+1)$^+$. The $^1$H NMR spectrum indicated the presence of two rotameric forms.

400 MHz NMR (CDCl$_3$) $\delta$0.93 (m, 3H) overlapping 0.96 (s, 9H), 1.34 (m, 2H), 1.63 (m, 2H), 3.37 (m, 2H), 3.46, 3.48 (overlapping s, total 1H), 4.61, 4.72 (s, total 2H), 7.25–7.7 (m, 11H), 8.15 (d, J=7.9 Hz, 1H).

Step H: 2-(Trifluoromethyl)phenyl N-Butyl-N-[[2'-(N-sulfamoyl)biphenyl-4-yl]methyl]carbamate A mixture of 37.2 mg (0.0661 mmole) of 2-(trifluoromethyl)phenyl N-butyl-N-[[2'-(N-t-butylsulfamoyl)biphenyl-4-yl]methyl]carbamate (from Step G), 72 $\mu$L of anisole, and 102 $\mu$L (151 mg, 1,32 mmole) of trifluoroacetic acid was stirred under N$_2$ at room temperature overnight. The solution then was evaporated under a stream of N$_2$. The resulting residue was dissolved in methylene chloride and applied to a 500-micron silica gel preparative TLC plate, which was developed in 3:1 hexane-EtOAc and visualized by UV light. The product band was isolated and extracted with 9:1 CH$_2$Cl$_2$—MeOH. Concentration of the extracts in vacuo yielded 22.6 mg (67%) of the title compound as a stiff, white foam, mp >45° C. (gradual); homogeneous by TLC (3:1 hexane-EtOAc); FAB-MS m/e 507 (M+1)$^+$. The $^1$H NMR spectrum indicated the presence of two rotameric forms.

400 MHz NMR (CDCl$_3$) $\delta$0.93 (m, 3H), 1.35 (m, 2H), 1.65 (m, 2H), 3.38, 3.43 (overlapping t, J$\simeq$7.5 Hz, total 2H), 4.13 (s, 2H), 4.61, 4.72 (s, total 2H), 7.25–7.7 (m, 11H), 8.15 (d, J=7.8 Hz, 1H).

Step I: 2-(Trifluoromethyl)phenyl N-Butyl-N-[[2'-[N-(2-chlorobenzoyl)sulfamoyl]biphenyl-4-yl]methyl]carbamate A mixture of 19 mg (0.12 mmole) of 1,1'-carbonyldiimidazole, 19 mg (0.12 mmole) of 2-chlorobenzoic acid, and 500 $\mu$L of dry THF was stirred under N$_2$ at 50° C. for 3 hours. Then a solution of 20 mg (0.0395 mmole) of 2-(trifluoromethyl)phenyl N-butyl-N-[[2'-(N-sulfamoyl)biphenyl-4-yl]methyl]carbamate and 17.5 $\mu$L (18 mg, 0.12 mmole) of DBU in 500 $\mu$L of dry THF was added. The mixture was maintained at 50° C. under N$_2$ overnight. The cooled mixture was partitioned between 3 mL of 5% citric acid (aqueous) and 5 mL of ethyl acetate. The organic layer was washed with water (2×5 mL), dried over sodium sulfate, filtered, and concentrated in vacuo. The residual semisolid was dissolved in methylene chloride and applied to a 500-micron silica gel preparative TLC plate, which was developed in 99:1 CH$_2$Cl$_2$—MeOH and visualized by UV light. The product band was isolated and extracted with 9:1 CH$_2$Cl$_2$—MeOH. Concentration of the extracts gave an oil, which still contained a minor impurity by TLC. Therefore, this material was flash chromatographed on silica gel to yield 21.8 mg (86%) of the title compound as a stiff, white foam, mp >150° C.

(gradual, preliminary softening); homogeneous by TLC in 99:1 CH$_2$Cl$_2$—MeOH; FAB-MS m/e 645 (M+1)$^+$. The $^1$H NMR spectrum indicated the presence of two rotameric forms.

400 MHz NMR (CDCl$_3$) δ0.93 (m, 3H), 1.33 (m, 2H), 1.55-1.7 (m, 2H), 3.26, 3.33 (t, J≈7.5 Hz, total 2H), 4.53, 4.63 (s, total 2H), 7.15-7.7 (m, 15H), 8.23, 8.31 (s, total 2H), 8.36 (d, J=8.0 Hz, 1H).

Analysis: (C$_{32}$H$_{28}$ClF$_3$N$_2$O$_5$S•H$_2$O): Calcd: C, 57.96; H, 4.56; N, 4.22. Found: C, 57.80; H, 4.18; N, 4.31.

EXAMPLE 2

1-Benzyl-3-[[2'-[N-(2-chlorobenzoyl)sulfamoyl]biphenyl-4-yl]methyl]-3-pentyl-1-phenylurea

Step A:
N-[[2'-(N-t-Butylsulfamoyl)biphenyl-4-yl]methyl]-N-pentylamine

By the procedure of Example 1, Step E, but substituting n-pentylamine for n-butylamine, the title compound was prepared in 37% yield as a white solid, mp 69°-70° C.; homogeneous by TLC (EtOAc); FAB-MS m/e 389 (M+1)$^+$.

400 MHz NMR (CDCl$_3$) δ0.88 (t, J=7.0 Hz, 3H), 0.97 (s, 9H), 1.25-1.35 (m, 4H), 1.53 (m, 2H), 2.63 (t, J=7.3 Hz, 2H), 3.58 (br s, 1H), 3.85 (s, 2H), 7.25-7.6 (m, 7H), 8.14 (dd, J=7.9, 1.3 Hz, 1H).

Step B:
N-[[2'-(N-t-Butylsulfamoyl)biphenyl-4-yl]methyl-N-pentylcarbamoyl chloride Following the procedure of Example 1, Step F, N-[[2'-(N-t-butylsulfamoyl)biphenyl-4-yl]methyl]-N-pentylamine (from Step A) was converted to the title compound in 52% yield as a white solid, mp 125°-126° C. (preliminary softening); homogeneous by TLC (3:1 hexane-EtOAc); FAB-MS m/e 451 (M+1)$^+$. The $^1$H NMR spectrum indicated the presence of two rotameric forms.

400 MHz NMR (CDCl$_3$) δ0.90 (m, 3H), 0.97 (s, 9H), 1.2-1.4 (m, 4H), 1.61 (m, 2H), 3.38 (m, 2H), 3.46 (s, 1H), 4.61, 4.74 (s, total 2H), 7.25-7.6 (m, 7H), 8.15 (d, J=7.8 Hz, 1H).

Analysis: (C$_{23}$H$_{31}$ClN$_2$O$_3$S); Calcd: C, 61.25; H, 6.93; N, 6.21. Found: C, 60.85; H, 7.02; N, 6.04.

Step C:
1-Benzyl-3-[[2'-(N-t-butylsulfamoyl)biphenyl-4-yl]methyl]-3-pentyl-1-phenylurea A mixture of 75 mg (0.166 mmole) of N-[[2'-(N-t-butylsulfamoyl)biphenyl-4-yl]methyl]-N-pentylcarbamoyl chloride (from Step B), 46 mg (0.25 mmole) of N-phenylbenzylamine, 58 μL (43 mg, 0.33 mmole) of N,N-diisopropylethylamine, and 1 mL of dry toluene was stirred under N$_2$ at 110° C. for 48 hours. The cooled reaction mixture was concentrated by rotary evaporation. Flash chromatography of the residual oil on silica gel (elution with 4:1 and then 3:1 hexane-EtOAc) gave 91 mg (92%) of the title compound as a tacky foam, homogeneous by TLC in 3:1 hexane-EtOAc; FAB-MS m/e 599 (M+1)$^+$.

400 MHz NMR (CDCl$_3$) δ0.80 (t, J=7.3 Hz, 3H), 0.94 (s, 9H), 1.00 (m, 2H), 1.16 (m, 2H), 1.28 (m, 2H), 2.98 (t, J=7.7 Hz, 2H), 3.45 (s, 1H), 4.34 (s, 2H), 4.79 (s, 2H), 7.0-7.6 (m, 17H) 8.14 (dd, J=8.0, 1.1 Hz, 1H).

Step D:
1-Benzyl-3-pentyl-1-phenyl-3-[[2'-(N-sulfamoyl)biphenyl-4-yl]methyl]urea A mixture of 88.7 mg (0.148 mmole) of 1-benzyl-3-butyl-3-[[2'-(N-t-butylsulfamoyl)biphenyl-4-yl]methyl]-1-phenylurea (from Step C), 160 μL (159 mg, 1.47 mmole) of anisole, and 660 μL (977 mg, 8.57 mmole) of anhydrous trifluoroacetic acid was stirred under N$_2$ at room temperature for 3 days and then evaporated to dryness under a stream of N$_2$. The residue was flash chromatographed on silica gel (elution with 3:1 and then 2:1 hexane-EtOAc) to yield 73.7 mg (92%) of the title compound as a stiff, white foam, homogeneous by TLC (3:1 hexane-EtOAc); FAB-MS m/e 543 (M+1)$^+$.

400 MHz NMR (CDCl$_3$) δ0.80 (t, J=7.3 Hz, 3H), 1.01 (m, 2H), 1.15 (m, 2H), 1.28 (m, 2H), 3.03 (t, J=7.7 Hz, 2H), 4.17 (s, 2H), 4.33 (s, 2H), 4.76 (s, 2H), 7.0-7.6 (m, 17H), 8.12 (d, J=7.9 Hz, 1H).

Step E:
1-Benzyl-3-[[2'-[N-(2-chlorobenzoyl)sulfamoy]biphenyl-4-yl]methyl]-3-pentyl-1-phenylurea By the procedure of Example 1, Step I, 1-benzyl-3-butyl-1-phenyl-3-[[2'-(N-sulfamoyl)biphenyl-4-yl]methyl]urea (from Step D) was acylated with 2-chlorobenzoic acid. The crude product was purified by flash chromatography on silica gel (elution with 3% and then 5% MeOH in CHCl$_3$) to give a 77% yield of the title compound as a stiff, white foam, mp >60° C. (gradual); homogeneous by TLC in 95:5 CH$_2$Cl$_2$—MeOH; FAB-MS m/e 680 (M+1)$^+$.

Analysis: (C$_{39}$H$_{38}$ClN$_3$O$_4$S•0.3CH$_2$Cl$_2$); Calcd: C, 66.88; H, 5.51; N, 5.96. Found: C, 66.71; H, 5.66; N, 5.76.

400 MHz NMR (CDCl$_3$) δ0.80 (t, J=7.3 Hz, 3H), 0.99 (m, 2H), 1.16 (m, 2H), 1.23 (m, 2H), 2.93 (t, J=7.7 Hz, 2H), 4.25 (s, 2H), 4.75 (s, 2H), 6.95-7.7 (m, 21H), 8.35 (d, J=7 Hz, 1H).

EXAMPLE 3

1-[N-[[2'-[N-(2-Chlorobenzoyl)sulfamoyl]biphenyl-4-yl]methyl]-N-pentylcarbamoyl]indoline

Step A
1-[N-[[2'-(N-t-Butylsulfamoyl)biphenyl-4-yl]-N-pentylcarbamoyl]indoline solution of 50 mg (0.11 mmole) of N-[[2'-(N-t-butylsulfamoyl)biphenyl-4-yl]methyl]-N-pentylcarbamoyl chloride (from Example 2, Step B), 12 mg (0.12 mmole) of triethylamine, and 20 mg (0.17 mmole) of indoline in 0.75 mL of toluene was stirred at 90° C. overnight. After cooling to room temperature, volatiles were removed in vacuo and the residue was flash chromatographed over silica gel (gradient elution using 10% to 20% EtOAc in hexane) to give the desired product quantitatively as an oil, homogeneous by TLC (4:1 hexane-EtOAc); FAB-MS m/e 534 (M+1)$^+$.

400 MHz NMR (CDCl$_3$) δ0.87 (t, J=7.0 Hz, 3H), 0.94 (s, 9H), 1.26 (m, 4H), 1.61 (m, 2H), 3.02 (t, J=8.3 Hz, 2H), 3.22 (t, J=7.4 Hz, 2H), 3.48 (s, 1H), 3.92 (t, J=8.3 Hz, 2H), 4.54 (s, 2H), 6.88 (t, J=7.5 Hz, 1H), 6.97 (d, J=7.7 Hz, 1H), 7.11-7.56 (m, 9H), 8.14 (d, J=8.0 Hz, 1H).

Step B:
1-[N-Pentyl-N-[(2'-sulfamoylbiphenyl-4-yl)methyl]carbamoyl]indoline

A solution of 59 mg (0.11 mmole) of 1-[N-[[2'-(N-t-butylsulfamoyl)biphenyl-4-yl]methyl]-N-pentylcarbamoyl]indoline (from Step A), 20 µL of anisole, and 0.5 mL of anhydrous TFA was stirred at room temperature for 16 hours. The residue obtained after evaporation of excess TFA was flash chromatographed over silica gel (elution with 0.5% MeOH—$CH_2Cl_2$) to give 49 mg (89%) of the title compound as a hard gum, homogeneous by TLC (95:5 MeOH—$CH_2Cl_2$); FAB-MS m/e 478 (M+1)+.

400 MHz NMR ($CDCl_3$) δ0.87 (t, J=6.9 Hz, 3H), 1.26 (m, 4H), 1.61 (m, 2H), 3.02 (t, J=8.3 Hz, 2H), 3.22 (t, J=7.3 Hz, 2H), 3.92 (t, J=8.3 Hz, 2H), 4.16 (s, 2H), 4.53 (s, 2H), 6.88 (t, J=7.4 Hz, 1H), 6.97 (d, J=8.0 Hz, 1H), 7.11–7.56 (m, 9H), 8.12 (dd, J=8.1, 1.7 Hz, 1H).

Step C:
1-[N-[[2'-[N-(2-Chlorobenzoyl)sulfamoyl]biphenyl-4-yl]methyl]-N-pentylcarbamoyl]indoline A solution of 21 mg (0.13 mmole) of 2-chlorobenzoic acid and 22 mg (0.13 mmole) of 1,1'-carbonyldiimidazole (CDI) in 0.8 mL of THF was stirred under $N_2$ at 65° C. for 2.5 hours. Subsequently, a solution of 32 mg (0.067 mmole) of 1-[N-pentyl-N-[(2'-sulfamoylbiphenyl-4-yl)methyl]carbamoyl]indoline (from Step B) and 20 µL (0.13 mmole) of 1,8-diazabicyclo[5.4.0]undec-7-ene (DBU) in 0.8 mL of THF was added. After stirring for 29 hours at 55° C., the mixture was partitioned between EtOAc and 5% citric acid (aqueous). The organic layer was washed with water and brine, then dried over sodium sulfate. After filtration and removal of volatiles, the crude product was flash chromatographed over silica gel (gradient elution with 0.5–1.0% MeOH in $CH_2Cl_2$) to give 28 mg (68%) of the title compound as an off-white solid, mp 83°–85° C.; homogeneous by TLC (95:5 MeOH—$CH_2Cl_2$); FAB-MS m/e 616 (M+1)+.

400 MHz NMR ($CDCl_3$) δ0.87 (t, J=7.1 Hz, 3H), 1.26 (m, 4H), 1.58 (m, 2H), 3.02 (t, J=8.2 Hz, 2H), 3.17 (t, J=7.4 Hz, 2H), 3.87 (t, J=8.2 Hz, 2H), 4.42 (s, 2H), 4.53 (s, 2H), 6.89 (t, J=7.3 Hz, 1H), 6.96 (d, J=8.1 Hz, 1H), 7.11–7.65 (m, 13H), 8.12 (d, J=7.7 Hz, 1H).

EXAMPLE 4
1-[N-[[2'-[N-(2-Chlorobenzoyl)sulfamoyl]biphenyl-4-yl]methyl]-N-pentylcarbamoyl]-1,2,3,4-tetrahydroquinoline

Step A:
1-[N-[[2'-(N-t-Butylsulfamoyl)biphenyl-4-yl]methyl]-N-pentylcarbamoyl]-1,2,3,4-tetrahydroquinoline A solution of 100 mg (0.22 mmole) of N-[[2'-(N-t-butylsulfamoyl)biphenyl-4-yl]methyl]-N-pentylcarbamoyl chloride (from Example 2, Step B), 0.2 mL (1.15 mmole) of N,N-diisopropylethylamine, and 44 mg (0.33 mmole) of 1,2,3,4-tetrahydroquinoline in 2.5 mL of toluene was stirred at 110° C. for two days. After cooling to room temperature, volatiles were removed by rotary evaporation, and the residue was flash chromatographed over silica gel (gradient elution using 10% to 12.5% EtOAc in hexane) to give 81 mg (66%) of the desired product as an oil, homogeneous by TLC (4:1 hexane-EtOAc), FAB-MS m/e 548 (M+1)+.

400 MHZ NMR ($CDCl_3$) δ0.86 (t, J=7.0 Hz, 3H), 0.95 (s, 9H), 1.24 (m, 4H), 1.56 (m, 2H), 1.88 (m, 2H), 2.69 (t, J=6.9 Hz, 2H), 3.16 (t, J=7.6 Hz, 2H), 3.57 (t, J=6.1 Hz, 2H), 4.42 (s, 2H), 6.8–7.6 (m, 11H), 8.14 (dd, J=7.8, 1.2 Hz, 1H).

Step B:
1-[N-Pentyl-N-[(2'-sulfamoylbiphenyl-4-yl)meth-yl]carbamoyl]-1,2,3,4-tetrahydroquinoline A solution of 86 mg (0.16 mmole) of 1-[N-[[2'-(N-t-butylsulfamoyl)biphenyl-4-yl]methyl]-N-pentylcarbamoyl]-1,2,3,4-tetrahydroquinoline (from Step A), 30 µL of anisole, and 0.8 mL of anhydrous TFA was stirred at room temperature for 16 hours. The residue obtained after evaporation of excess TFA was flash chromatographed over silica gel (elution with 0.5% MeOH in $CH_2Cl_2$) to give 55 mg (71%) of the title compound as an off-white foam, homogeneous by TLC (95:5 MeOH$CH_2Cl_2$), FAB-MS m/e 492 (M+1)+.

400 MHz NMR ($CDCl_3$) δ0.86 (t, J=7.0 Hz, 3H), 1.24 (m, 4H), 1.56 (m, 2H), 1.85 (m, 2H), 2.69 (t, J=6.7 Hz, 2H) 3.20 (t, J=7.4 Hz, 2H), 3.55 (t, J=6.1 Hz, 2H), 4.13 (s, 1H), 4.41 (s, 2H), 6.85–7.10 (m, 11H), 8.14 (d, J=9.0 Hz, 1H).

Step C:
1-[N-[[2'-[N-(2-Chlorobenzoyl)sulfamoyl]biphenyl-4-yl]-methyl]-N-pentylcarbamoyl]-1,2,3,4-tetrahydroquinoline The title compound was prepared from 2-chlorobenzoic acid (2.0 equivalents), CDI (2.0 equiv), 1-[N-pentyl-N-[(2'-sulfamoylbiphenyl-4-yl)methyl]carbamoyl]-1,2,3,4-tetrahydroquinoline (from Step B) (1.0 equiv), and DBU (2.0 equiv), according to the procedure of Example 3, Step C, to give a 78% yield of the desired material after flash chromatography as an off-white solid, mp 71°–74° C.; homogeneous by TLC in 9:1 $CH_2Cl_2$—MeOH; FAB-MS m/e 630 (M+1)+.

400 MHz NMR ($CDCl_3$) δ0.86 (t, J=7.2 Hz, 3H), 1.17 (m, 2H), 1.25 (m, 2H), 1.52 (m, 2H), 1.84 (m, 2H), 2.67 (t, J=6.6 Hz, 2H), 3.10 (t, J=7.0 Hz, 2H), 3.51 (t, J=6.1 Hz, 2H), 4.32 (s, 2H), 6.87–7.65 (m, 15H), 8.34 (dd, J=8.0, 1.4 Hz, 1H).

EXAMPLE 5
1-[N-Butyl-N-[[2'-[N-(2-chlorobenzoyl)sulfamoyl]-biphenyl-4-yl]methyl]carbamoyl]-1,2,3,4-tetrahydroquinoline

Step A:
1-[N-Butyl-N-[[2'-(N-t-butylsulfamoyl)biphenyl-4-yl]methyl]carbamoyl]-1,2,3,4-tetrahydroquinoline The title compound was prepared from N-butyl-N-[[2'-(N-t-butylsulfamoyl)biphenyl-4-yl]methyl]carbamoyl chloride (from Example 4, Step A), N,N-diisopropylethylamine, and 1,2,3,4-tetrahydroquinoline in toluene, according to the procedure of Example 4, Step A, to give 93% yield of the desired material after flash chromatography as a foam, homogeneous by TLC in 4:1 hexane-EtOAc; FAB-MS m/e 534 (M+1)+.

200 MHz NMR ($CDCl_3$) δ0.89 (t, J=7.1 Hz, 3H), 0.98 (s, 9H), 1.22 (m, 2H), 1.57 (m, 2H), 1.90 (m, 2H), 2.71 (t, J=6.6 Hz, 2H), 3.20 (t, J=7.4 Hz, 2H), 3.51 (s, 1H), 3.59 (t, J=6.0 Hz, 2H), 4.44 (s, 2H), 6.85–7.65 (m, 11H), 8.16 (dd, J=7.6, 1.8 Hz, 1H).

Step B:

1-[N-Butyl-N-[(2'-sulfamoylbiphenyl-4-yl)methyl]carbamoyl]-1,2,3,4-tetrahydroquinoline The title compound was prepared from 1-[N-butyl-N-[[2'-(N-t-butylsulfamoyl)biphenyl-4-yl]methyl]carbamoyl]-1,2,3,4-tetrahydroquinoline (from Step A) and TFA in the presence of anisole, according to the procedure of Example 4, Step B, to give a 97% yield of the desired material after flash chromatography as a foam, homogeneous by TLC in 95:5 $CH_2Cl_2$—MeOH; FAB-MS m/e 478 $(M+1)^+$.

400 MHz NMR ($CDCl_3$) δ0.87 (t, J=7.4 Hz, 3H), 1.25 (m, 2H), 1.57 (m, 2H), 1.85 (m, 2H), 2.67 (t, J=6.6 Hz, 2H), 3.20 (t, J=7.5 Hz, 2H), 3.55 (t, J=6.1 Hz, 2H), 4.13 (s, 2H), 4.41 (s, 2H), 6.88 (t, J=6.3 Hz, 1H) 6.90–7.60 (m, 11H), 8.14 (dd, J=7.9, 1.2 Hz, 1H).

Step C: 1-[N-Butyl-N-[[2'-[N-(2-chlorobenzoyl)sulfamoyl]biphenyl-4-yl]methyl]carbamoyl]-1,2,3,4-tetrahydroquinoline The title compound was prepared from 2-chlorobenzoic acid (2.5 equivalents), CDI (2.5 equiv), 1-[N-butyl-N-[(2'-sulfamoylbiphenyl-4-yl)methyl]carbamoyl]-1,2,3,4-tetrahydroquinoline (from Step B) (1.0 equiv), and DBU (2.5 equiv), according to the procedure of Example 3, Step C, to give an 83% of the desired material after flash chromatography as an off-white solid, mp 80°–82° C.; homogeneous by TLC in 95:5 $CH_2Cl_2$—MeOH; FAB-MS m/e 616 $(M+1)^+$.

400 MHz NMR ($CDCl_3$) δ0.86 (t, J=7.3 Hz, 3H), 1.22 (m, 2H), 1.51 (m, 2H), 1.84 (m, 2H), 2.67 (t, J=7.0 Hz, 2H), 3.12 (t, J=7.4 Hz, 2H), 3.52 (t, J=6.1 Hz, 2H), 4.32 (s, 2H), 6.85–7.70 (m, 15H), 8.34 (dd, J=7.9, 1.4 Hz, 1H), 8.51 (s, 1H).

EXAMPLE 6

1-[N-[[2'-[N-(t-Butoxycarbonyl)sulfamoyl]biphenyl-4-yl]methyl]-N-butylcarbamoyl]-1,2,3,4-tetrahydroquinoline A mixture of 40 mg (0.84 mmole) of 1-[N-butyl-N-[(2'-sulfamoylbiphenyl-4-yl)methyl]carbamoyl]-1,2,3,4-tetrahydroquinoline (from Example 5, Step B) and 5.0 mg (0.21 mmole) of sodium hydride was stirred at 50° C. for 3 hours. After adding 37 mg (0.17 mmole) of di-t-butyl dicarbonate, stirring was continued at 50° C. for 2 days. Then the reaction mixture was treated with methanolic 1N HCl and filtered. The residue obtained after evaporation of volatiles was flash chromatographed over silica gel (gradient elution using 0.5–1.0% MeOH in $CH_2Cl_2$), followed by HPLC purification on a Zorbax C8 Semiprep reversed phase column (55:45 MeCN—$H_2O$, containing 0.1% TFA) to give 18 mg (37%) of the title compound as a stiff foam, mp>67° C. (gradual); homogeneous by TLC in 95:5 $CH_2Cl_2$—MeOH; FAB-MS m/e 578 $(M+1)^+$.

400 MHz NMR ($CDCl_3$) δ0.88 (t, J=7.3 Hz, 3H), 1.22 (m, 2H), 1.28 (s, 9H), 1.55 (m, 2H), 1.83 (m, 2H), 2.65 (t, J=6.8 Hz, 2H), 3.23 (t, J=7.5 Hz, 2H), 3.53 (m, 2H), 4.41 (s, 2H), 6.35 (s, 1H), 6.85–7.70 (m, 15H), 8.22 (dd, J=8.0, 1.3 Hz, 1H).

EXAMPLE 7

1-Butyl-1-[[2'-[N-(2-chlorobenzoyl)sulfamoyl]biphenyl-4-yl]methyl]-3-methyl-3-[2-(trifluoromethyl)phenyl]urea

Step A:
N-Methyl-N-[2-(trifluoromethyl)phenyl]carbamoyl Chloride

A mixture of 1.00 g (5.71 mmole) of 2-(methylamino)benzotrifluoride, 9 mL (17.3 mmole) of 1.93M phosgene in toluene, and 10 mL of toluene was stirred under $N_2$ for a hour and then treated with 20 mL of 2.5N sodium hydroxide (aqueous). The layers were separated, and the organic phase was concentrated in vacuo to yield 1.12 g (83%) of the title compound as a clear oil, which eventually solidified after prolonged standing: mp 44°–46° C.; homogeneous by TLC in 3:1 hexane-EtOAc; IR spectrum $\nu_{CO}$ 1750 cm$^{-1}$; FAB-MS m/e 237 $(M+1)^+$.

400 MHz NMR ($CDCl_3$) δ3.32 (s, 3H), 7.34 (d, J=7.5 Hz), 7.54 (dd, J≈7.5, 7.5 Hz), 7.65 (dd, J≈7.5, 7.5 Hz), 7.75 (d, J=7.3 Hz).

Step B:
1-Butyl-1-[[2'(N-t-butylsulfamoyl)biphenyl-4-yl]methyl]-3-methyl-3-[2-trifluoromethyl)phenyl]urea A mixture of 75 mg (0.2 mmole) of N-butyl-N-[[2'-(N-t-butylsulfamoyl)biphenyl-4-yl]methyl]amine (from Example 1, Step E), 32 mg (0.134 mmole) of N-methyl-N-[2-(trifluoromethyl)phenyl]carbamoyl chloride (from Step A), 62 μL (46 mg 0.36 mmole) of N,N-diisopropylethamine, and 300 μL of dry toluene was stirred under $N_2$ at 110° C. for 24 hours. The cooled mixture was concentrated in vacuo, and the residue was flash chromatographed on silica gel (gradient elution with 4:1 to 1:1 hexane-EtOAc). Evaporation of the product fractions gave 75.0 mg (98%) of the title compound as a white foam, which became tacky upon standing; homogeneous by TLC in 3:1 hexane-EtOAc; FAB-MS m/e 577 $(M+1)^+$.

400 MHz NMR ($CDCl_3$) δ0.77 (t, J=7.3 Hz, 3H), 0.94 (s, 9H), 1.07 (m, 2H), 1.23 (m, 2H), 2.99 (t, J=7.9 Hz, 2H), 3.45 (s, 1H), 4.36 (s, 2H), 7.2–7.7 (m, 11H), 8.14 (dd, J=7.9, 1.3 Hz).

Step C:
1-Butyl-3-methyl-1-[(2'-sulfamoylbiphenyl-4-yl)methyl]-3-[2-(trifluoromethyl)phenyl]urea The title compound was prepared from 1-butyl-1-[[2'-(N-t-butylsulfamoyl)biphenyl-4-yl]methyl]-3-methyl-3-[2-(trifluoromethyl)phenyl]urea (from Step B) according to the procedure of Example 2, Step D. Purification of the crude product by flash chromatography (elution with 2:1 and then 1:1 hexane-EtOAc) afforded a 76% yield of a stiff, white foam, which became tacky upon standing; homogeneous by TLC (3:1 hexane-EtOAc); FAB-MS m/e 521 $(M+1)^+$.

400 MHz NMR ($CDCl_3$) δ0.76 (t, J=7.3 Hz, 3H), 1.06 (m, 2H), 1.21 (m, 2H), 3.01 (t, J=7.9 Hz, 2H), 3.13 (s, 3H), 4.22 (br s, 2H), 4.37 (s, 2H), 7.15–7.7 (m, 11H), 8.12 (dd, J=7.9, 1.2 Hz, 1H).

Analysis: ($C_{26}H_{28}F_3N_3O_3S$): Calcd: C, 60.10; H, 5.43; N, 8.09. Found: C, 59.77; H, 5.73; N, 7.75.

Step D:
1-Butyl-1-[[2'-[N-(2-chlorobenzoyl)sulfamoyl]biphenyl-4-yl]methyl]-3-methyl-3-[2-(trifluoromethyl)phenyl]urea Following the procedure of Example 1, Step I, 1-butyl-3-methyl-1-[(2'-sulfamoylbiphenyl-4-yl)methyl]-3-[2-(trifluoromethyl)phenyl]urea was acylated with 2-chlorobenzoic acid. After work-up, the crude product was purified initially by flash chromatography on silica gel (elution with 2% and then 5% MeOH in $CH_2Cl_2$). Further purification by HPLC on a Zorbax C8 Semi-prep reversed phase column (70:30 MeCN—$H_2O$, containing 0.1% TFA) provided a 29% yield of the title compound as a stiff, white foam, mp>60° C. (gradual); homogeneous by TLC (95:5 $CH_2Cl_2$—MeOH); FAB-MS m/e 658 (M+1)+.

400 MHz NMR ($CDCl_3$) δ0.77 (t, J=7.3 Hz, 3H), 1.05 (m, 2H), 1.19 (m, 2H), 2.94 (t, J=7.9 Hz, 2H), 3.12 (s, 3H), 4.30 (s, 2H), 7.05-7.7 (m, 15H), 8.35 (dd, J=7.9, 1.3 Hz, 1H), overlapping 8.38 (s, 1H).

Analysis: ($C_{33}H_{31}ClF_3N_3O_4S$•0.6$H_2O$): Calcd: C, 59.25; H, 4.85; N, 6.28. Found: C, 59.00; H, 4.59; N, 5.96.

EXAMPLE 8

1-[N-Pentyl-N-[[2'-(1H-tetrazol-5-yl)biphenyl-4-yl]methyl]carbamoyl]-1,2,3,4-tetrahydroquinoline

Step A: 1,2,3,4-Tetrahydroquinoline-1-carbonyl Chloride

By the procedure of Example 7, Step A, 1,2,3,4-tetrahydroquinoline was reacted with phosgene to give a 90% yield of the title compound as a dark orange oil, homogeneous by TLC (3:1 hexane-EtOAc) but $R_f$identical to that of starting material; IR spectrum $\nu_{CO}$ 1740 cm$^{-1}$; FAB-MS m/e 196 (M+1)+.

200 MHz NMR ($CDCl_3$) δ2.05 (m, 2H), 2.82 (t, J=6.4 Hz), 3.95 (t, J=6.3 Hz), 7.1-7.3 (m, 3H), 7.65 (d, J=7.7 Hz, 1H).

Step B:
N-Pentyl-N-[[2'-(N-trityltetrazol-5-yl)biphenyl-4-yl]methyl]amine

A mixture of 10.0 g (16.5 mmole) of 5-[4'-(bromomethyl)biphenyl-2-yl]-N-trityltetrazole [P. E. Aldrich, M. E. Pierce, and J. J. V. Duncia, European Patent Application 291,969 (1988)], 9.5 mL (7.14 g, 8.2 mmole) of n-pentylamine, 2.8 mL (2.03 g, 20 mmole) of triethylamine, and 100 mL of dry methylene chloride was stirred under $N_2$ at room temperature overnight. Next, the mixture was shaken with 100 mL of 0.25M citric acid (aqueous). The organic layer was dried over sodium sulfate, filtered, and concentrated in vacuo. The viscous oil was flash chromatographed on silica gel (elution initially with 1:1 hexane-EtOAc and then with a larger volume of EtOAc alone) to yield 4.57 g (49%) of the title compound as a very viscous oil, homogeneous by TLC (EtOAc); FAB-MS m/e 563 (M+1)+.

400 MHz NMR ($CDCl_3$) δ0.86 (t, J=Hz, 3H), 1.2-1.35 (m, 4H), 1.49 (m, 2H), 2.58 (t, J=7.3 Hz, 2H), 3.69 (s, 2H), 6.85-7.5 (m, 22H), 7.91 (dd, J=7.2, 1.8 Hz).

Step C:
1-[N-Pentyl-N-[[2'-(N-trityltetrazol-5-yl)biphenyl-4-yl]methyl]carbamoyl]-1,2,3,4-tetrahydroquinoline Following the procedure of Example 7, Step B, 1,2,3,4-tetrahydroquinoline-1-carbonyl chloride (from Step A) was reacted with 1.2 equivalents of N-pentyl-N-[[2'-(N-trityltetrazol-5-yl)biphenyl-4-yl]methyl]amine (from Step D) in the presence of N,N-diisopropylethylamine. Flash chromatography of the crude product on silica gel (elution with 4:1 and then 3:1 hexane-EtOAc) gave two major products. (Concentration of fractions containing the pure second product afforded a 27% yield of the title compound as a stiff foam, homogeneous by TLC in 3:1 hexane-EtOAc; FAB-MS m/e 723 (M+1)+. The $^1$H NMR spectrum indicated the presence of two isomeric forms.

400 MHz NMR ($CDCl_3$) δ0.84 (m, 3H), 1.1-1.3 (m, 4H), 1.45-1.6 (m, 2H), 1.7-1.85 (m, 2H), 2.5-2.7 (m, 2H), 3.10, 3.18 (t, J≈Hz, total 2H), 3.48 (m, 2H), 4.23, 4.35 (s, total 2H), 6.8-7.6 (m, 26H), 7.88, 8.34 (d, J≈8 Hz, total 1H).

Step D:
1-[N-Pentyl-N-[[2'-(1H-tetrazol-5-yl)biphenyl-4-yl]methyl]carbamoyl]tetrahydroquinoline A mixture of 29.3 mg (0.405 mmole) of 1-[N-pentyl-N-[[2'-(N-trityltetrazol-5-yl)biphenyl-4-yl]methyl]carbamoyl]-1,2,3,4-tetrahydroquinoline (from Step E), 400 μL of glacial acetic acid, and 180 μL of $H_2O$ was stirred under $N_2$ at 60° C. for 16 hours, then cooled, and concentrated to dryness in vacuo. The residual oil was flash chromatographed on silica gel (elution with 3% and then 5% MeOH in $CH_2Cl_2$) to yield 6.0 mg (31%) of the title compound as a stiff foam, homogeneous by TLC (95:5 $CH_2Cl_2$—MeOH); FAB-MS m/e 481 (M+1)+.

400 MHz NMR ($CDCl_3$) δ0.84 (t, J=7.2 Hz, 3H), 1.16 (m, 2H), overlapping 1.23 (m, 2H), 1.52 (m, 2H), 1.77 (m, 2H), 2.60 (t, J=6.6 Hz, 2H), 3.14 (t, J≈7 Hz, 2H), 3.43 (t, J=6.1 Hz, 2H), 4.30 (s, 2H), 6.8-7.6 (m, 11H), 7.94 (dd, J=7.8, 1.2 Hz, 1H).

EXAMPLE 9

1-Methyl-3-pentyl-3-[[2'-(1H-tetrazol-5-yl)biphenyl-4-yl]methyl]-1-[2-(trifluoromethyl)phenyl]urea

Step A:
1-Methyl-3-pentyl-1-[2-(trifluoromethyl)phenyl]-3-[[2'-(N-trityltetrazol-5-yl)biphenyl-4-yl]-methyl]urea Following the procedure of Example 7, Step B, N-methyl-N-[2-(trifluoromethyl)phenyl]carbamoyl chloride (from Example 7, Step A) was reacted with 1.2 equivalents of N-pentyl-N-[[2'-(N-trityltetrazol-5-yl)biphenyl-4-yl]methyl]amine (from Step D) in the presence of N,N-diisopropylethylamine. Flash chromatography of the crude product on silica gel (elution with 4:1 and then 3:1 hexane-EtOAc) gave two major products. Concentration of fractions containing the pure second product afforded a 26% yield of the title compound as a stiff foam, homogeneous by TLC in 3:1 EtOAc); FAB-MS m/e 772 (M+Li)+. The $^1$H NMR spectrum indicated the presence of two isomeric forms.

400 MHz NMR ($CDCl_3$) δ0.76, 0.80 (t, J=7.3 Hz, total 3H), 0.85-1.3 (complex m, 6H), 2.86, 3.04 (t, J=8 Hz, total 2H), 3.10, 3.13 (s, total 3H), 4.25, 4.34 (s, total 2H), 6.85-7.7 (m, 26H), 7.88, 8.34 (d, J=7 Hz, total 1H).

Step B:
1-Methyl-3-pentyl-3-[[2'-(1H-tetrazol-5-yl)biphenyl-4-yl]methyl]-1-[2-(trifluoromethyl)phenyl]urea By the procedure of Example 8, Step D, 1-methyl-3-pentyl-1-[2-(trifluoromethyl)phenyl]-3-[[2'(N-trityltetrazol-5-yl)biphenyl-4-yl]methyl]urea (from Step A) was deprotected with aqueous acetic acid. The residual oil was flash chromatographed on silica gel (elution with 3% and then 5% MeOH in CH₂Cl₂) to give a 31% yield of the title compound as a stiff foam, homogeneous by TLC (95:5 CH₂Cl₂-MeOH); FAB-MS m/e 523 (M+1).

200 MHz NMR (CDCl₃) δ0.80 (t, J=7.1 Hz, 3H), 0.95-1.35 (complex m, 6H), 3.01 (t, J=7.8 Hz, 2H), 3.09 (s, 3H), 4.29 (s, 2H), 7.05-7.7 (m, 11H), 7.99 (dd, J≈7.5, 1.5 Hz, 1H).

Additional compounds made by the above procedures described in Examples 1-9 are tabulated in Table II below:

TABLE II

| | q | R | mp. | formula | Analysis C | H | N |
|---|---|---|---|---|---|---|---|
| (1)[a] | 4 | 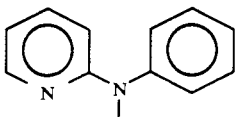 | >50° C. (gradual) | C₃₃H₃₀ClF₃N₂O₅S.0.7H₂O | Calcd: 59.04 Found: 58.64 | 4.65 4.27 | 4.17 4.47 |
| (2)[b] | 3 | 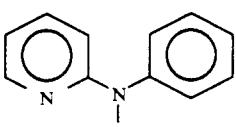 | >75° C. (gradual) | C₃₆H₃₃ClN₄O₄S.H₂O | Calcd: 64.42 Found: 64.22 | 5.26 5.10 | 8.35 8.11 |
| (3)[b] | 4 | 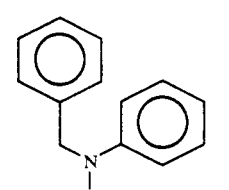 | >70° C. (gradual) | C₃₇H₃₅ClN₄O₄S.0.7H₂O | Calcd: 65.34 Found: 65.06 | 5.40 5.30 | 8.24 7.94 |
| (4)[b] | 3 | 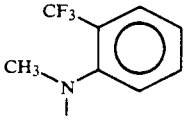 | >60° C. (gradual) | C₃₈H₃₆ClN₃O₄S.0.4CH₂Cl₂ | Calcd: 65.87 Found: 65.80 | 5.30 5.15 | 6.00 6.19 |
| (5)[c] | 4 | 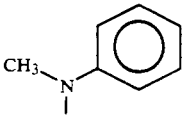 | 156-158° C. | C₃₄H₃₃ClF₃N₃O₄S.0.5H₂O | Calcd: 59.95 Found: 59.81 | 5.03 4.78 | 6.17 5.88 |
| (6)[c] | 4 | 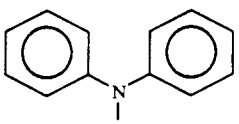 | >55° C. (gradual) | C₃₃H₃₄ClN₃O₄S.0.7H₂O | Calcd: 64.26 Found: 64.02 | 5.79 5.61 | 6.81 6.50 |
| (7)[c] | 4 | | 161-163° C. | C₃₈H₃₆ClN₃O₄S.0.1H₂O | Calcd: 68.32 Found: 68.04 | 5.46 5.27 | 6.29 6.27 |

TABLE II-continued

[Structure: CH₃(CH₂)q-N(C(=O)R)-CH₂-[phenyl]-[phenyl]-SO₂NHC(=O)-[chlorophenyl with Cl]]

| q | R | mp. | formula | Analysis C | H | N |
|---|---|---|---|---|---|---|
| (8)^{c,d} 4 | [S-containing bicyclic amine, thiomorpholine fused with benzene, N-substituted] | >65° C. (gradual) | C₃₄H₃₄ClN₃O₄S₂·H₂O | Calcd: 61.29 Found: 61.27 | 5.45 5.14 | 6.31 5.92 |
| (9)^{c,e} 4 | [carbonyl-containing bicyclic amine, dihydroquinolinone, N-substituted] | 148–149° C. | C₃₅H₃₄ClN₃O₅S·0.2H₂O | Calcd: 64.79 Found: 64.46 | 5.50 5.25 | 6.48 6.53 |
| (10)^{c,f} 4 | [chloro-substituted diarylamine with pyridine N, N-substituted] | >60° C. (gradual) | C₃₇H₃₄Cl₂N₄O₄S·1.1CH₂Cl₂ | Calcd: 57.55 Found: 57.19 | 4.59 4.42 | 7.05 6.70 |

FOOTNOTES TO TABLE II
^{a}Refer to Example 1 for analogous procedure.
^{b}Refer to Example 2 for analogous procedure.
^{c}Refer to Example 7 for analogous procedure.
^{d}For synthesis of amine: C. Angelini, G. Grandolini, and L. Mignini, Ann. Chim. (Rome), 46, 235 (1956).
^{e}For synthesis of amine: G. R. Clemo and W. H. Perkin, Jr., J. Chem. Soc., 1608 (1924).
^{f}For synthesis of amine: Deutsche Gold- und Silber-Scheideanstalt vorm. Roessler, Netherlands Patent Appl. 6,511,104 (1966).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| Compound | 50 |
| Lactose | 149 |
| Magnesium stearate | 1 |
| Capsule (size No. 1) | 200 |

The Compound (title compound of Example 4) can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain the Compound (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of the Compound (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain the Compound (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain the Compound (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

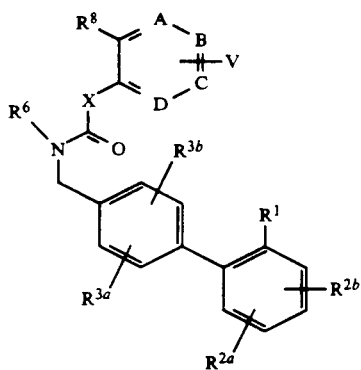

or a pharmaceutically acceptable salt thereof wherein:

A, B, C, and D are independently —CH= or —N=, with the proviso that at least two of them are —CH=;

X is —O— or —N($R^7$)—;

$R^1$ is
- (a) —$CO_2R^4$,
- (b) —$SO_3R^5$,
- (c) —$NHSO_2CF_3$,
- (d) —$PO(OR^5)_2$,
- (e) —$SO_2$—NH—$R^9$,
- (f) —$CONHOR^5$,
- (g) —$SO_2$NH-heteroaryl,
- (h) —$CH_2SO_2$NH-heteroaryl,
- (i) —$SO_2$NHCO$R^{23}$,
- (j) —$CH_2SO_2$NHCO$R^{23}$,
- (k) —CONHSO$_2R^{23}$,
- (l) —$CH_2$CONHSO$_2R^{23}$,
- (m) —NHSO$_2$NHCO$R^{23}$,
- (n) —NHCONHSO$_2R^{23}$,
- (o) —SO$_2$NHSO$_2R^{23}$,
- (p) —SO$_2$NHCO$_2R^{20}$,
- (q) —SO$_2$NHCONH$R^{20}$, (r) 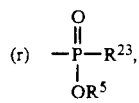

(s) 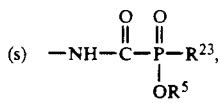

(t) 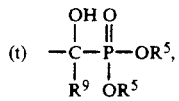

(u) 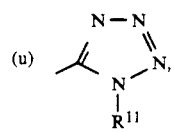

(v) 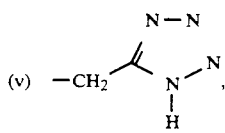

(w) 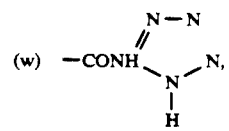

(x) —CONHNHSO$_2$CF$_3$, (y) 

(z) 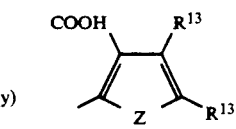

(aa) 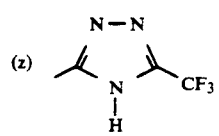

(bb) 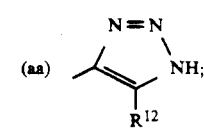

wherein:

Y is
- (1) —$CO_2R^4$,
- (2) —$SO_3R^5$,
- (3) —NHSO$_2$CF$_3$,
- (4) —PO(OR$^5$)$_2$, or
- (5) —SO$_2$—NH—$R^9$;
- (6) 1H-tetrazol-5-yl;

$R^{2a}$ and $R^{2b}$ are each independently:
- (a) hydrogen,
- (b) halo,
- (c) —NO$_2$,
- (d) —NH$_2$,
- (e) C$_1$-C$_4$-alkylamino,
- (f) —SO$_2$NHR$^9$,
- (g) —CF$_3$,
- (h) C$_1$-C$_4$-alkyl
- (i) C$_1$-C$_4$-alkoxy;

$R^{3a}$ is
- (a) —H,
- (b) halo,
- (c) C$_1$-C$_6$-alkyl,
- (d) C$_1$-C$_6$-alkoxy,
- (e) C$_1$-C$_6$-alkoxy-C$_1$-C$_4$-alkyl;

$R^{3b}$ is
- (a) —H,
- (b) —halo,
- (c) —NO$_2$,
- (d) C$_1$-C$_6$-alkyl,
- (e) C$_1$-C$_5$-alkylcarbonyloxy,
- (f) C$_3$-C$_6$-cycloalkyl
- (g) C$_1$-C$_6$-alkoxy,
- (h) —NHSO$_2R^4$,
- (i) hydroxy-C$_1$-C$_4$-alkyl,
- (j) aryl-C$_1$-C$_4$-alkyl
- (k) C$_1$-C$_4$-alkylthio (l) $C_1$-$C_4$-alkylsulfinyl
(m) $C_1$-$C_4$-alkylsulfonyl
(n) —$NH_2$
(o) $C_1$-$C_4$-alkylamino
(p) di($C_1$-$C_4$-alkyl)amino
(q) —$CF_3$
(r) —$SO_2$—$NHR^9$
(s) aryl;
(t) furyl;

$R^4$ is H, $C_1$-$C_6$-alkyl, —$CH_2$-aryl or aryl;

$R^5$ is H or —$CH(R^4)$—O—CO—$R^{4a}$ wherein $R^{4a}$ is $C_1$-$C_6$-alkyl, aryl or —$CH_2$-aryl;

$R^6$ is (a) $C_1$-$C_6$-alkyl, $C_2$-$C_6$-alkenyl or $C_2$-$C_6$-alkynyl each of which is unsubstituted or substituted with one or more substituents selected from the group consisting of aryl, $C_3$-$C_7$-cycloalkyl, halo, $C_1$-$C_4$-alkoxy, —$NH_2$, —NH($C_1$-$C_4$-alkyl), —N(-$C_1$-$C_4$-alkyl)$_2$, —NH—$SO_2R^4$, —$COOR^4$, —$SO_2NHR^9$, and $C_1$-$C_4$-alkylthio, (b) $C_3$-$C_7$-cycloalkyl unsubstituted or substituted with one or more substituents selected from the group consisting of $C_1$-$C_4$-alkyl, $C_1$-$C_4$-alkoxy, $C_1$-$C_4$-alkylthio, OH, perfluoro-$C_1$-$C_4$-alkyl, and halo, (c) $C_3$-$C_7$-cycloalkyl-$C_1$-$C_3$-alkyl wherein the cycloalkyl is unsubstituted or substituted as in (b) above, (d) aryl, or (e) heteroaryl;

$R^7$ is (a) H, (b) phenyl unsubstituted or substituted with 1 or 2 substituents selected from the group consisting of halo, $C_1$-$C_4$-alkoxy, $C_1$-$C_4$-alkyl, —$NO_2$, —$CF_3$, —$SO_2NR^9R^{10}$, $C_1$-$C_4$-alkylthio, —OH, —$NH_2$, —$COOR^4$, $C_3$-$C_7$-cycloalkyl, and $C_3$-$C_{10}$-alkenyl, (c) $C_1$-$C_6$-alkyl, $C_2$-$C_6$-alkenyl or $C_2$-$C_6$-alkynyl each of which is unsubstituted or substituted with one or more substituents selected from the group consisting of aryl, heteroaryl, $C_3$-$C_7$-cycloalkyl, halo, $C_1$-$C_4$-alkoxy, —$NH_2$, —NH(-$C_1$-$C_4$-alkyl), —N($C_1$-$C_4$-alkyl)$_2$, —NH—$SO_2R^4$, —$COOR^4$, —$SO_2NHR^9$, and $C_1$-$C_4$-alkylthio, (d) heteroaryl, or (e) $C_3$-$C_7$-cycloalkyl unsubstituted or substituted with one or more substituents selected from the group consisting of $C_1$-$C_4$-alkyl, $C_1$-$C_4$-alkoxy, $C_1$-$C_4$-alkylthio, —OH, —$COOR^4$, perfluoro-$C_1$-$C_4$-alkyl, and halo;

$R^8$ is —H, halo, —$CF_3$, —$CH_3$, —$OCH_3$ or —$NO_2$;

$R^7$ and $R^8$ when joined together form a ring with the atoms to which they are attached such that $R^7$-$R^8$ is (a) —Y—$(CH_2)_n$—Z, wherein n is 1 or 2; Y is a single bond, —C(O)— or —$C(R^{14})(R^{15})$—; Z is a single bond, —O—, —$S(O)_p$—, —$N(R^{16})$—, —C(O)—, —$CF_2$— or —$C(R^{14})(R^{15})$—; and p is 0, 1 or 2

(b)

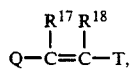

with the proviso that:
(1) Q is a single bond or —CO—;
(2) T is a single bond or —CO—; and
(3) at least one of Q and T is a single bond, (c)

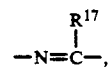

(d)

(e) 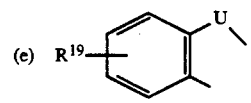

wherein U is —O—, —S—, —C(O)—, —$CF_2$— or —$CH_2$—, or (f) 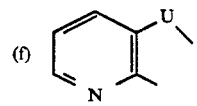

$R^9$ is H, $C_1$-$C_5$-alkyl, aryl or —$CH_2$-aryl;
$R^{10}$ is H, $C_1$-$C_4$-alkyl, or
$R^9$ and $R^{10}$ when together form —$(CH_2)_m$— where m is 3–6;
$R^{11}$ is H, $C_1$-$C_6$-alkyl, $C_2$-$C_4$-alkenyl, $C_1$-$C_4$-alkoxy-$C_1$-$C_4$-alkyl, or —$CH_2$—$C_6H_4R^{21}$;
$R^{12}$ is —CN, —$NO_2$ or —$CO_2R^4$;
$R^{13}$ is H, $C_2$-$C_4$-alkanoyl, $C_1$-$C_6$-alkyl, allyl, $C_3$-$C_6$-cycloalkyl, phenyl or benzyl;
$R^{14}$ and $R^{15}$ are independently H, $C_1$-$C_4$-alkyl, aryl, aryl-$C_1$-$C_2$-alkyl, $C_1$-$C_4$-alkoxycarbonyl, —$CO_2H$ or —$CH_2OH$;
$R^{16}$ is (a) $C_1$-$C_6$-alkyl, either unsubstituted or substituted with $C_1$-$C_4$-alkoxy, $C_1$-$C_4$-alkyl-$S(O)_p$—, —$CF_3$, —OH, —CN, $C_1$-$C_4$-alkoxycarbonyl, —$CO_2H$, —$CONR^9R^{10}$ or —CO-aryl,
(b) $C_3$-$C_6$-alkenyl,
(c) $C_3$-$C_6$-cycloalkyl,
(d) aryl,
(e) heteroaryl,
(f) —$COR^{20}$,
(g) —$CO_2R^{20}$,
(h) —$CONR^9R^{10}$, or
(i) —$SO_2R^{20}$;
$R^{17}$ and $R^{18}$ are independently H, $C_1$-$C_4$-alkyl, aryl, aryl-$C_1$-$C_2$-alkyl, $C_1$-$C_4$-alkoxy, —$CF_3$, halo, $C_1$-$C_4$-alkoxycarbonyl, —$CO_2H$ or —$CH_2OH$;
$R^{19}$ is $C_1$-$C_4$-alkyl, $C_1$-$C_4$-alkoxy, halo, —$CF_3$, $C_1$-$C_4$-alkyl-$S(O)_p$—, $CF_3SO_2$—, —CN, —$NO_2$, $C_1$-$C_4$-alkoxycarbonyl, —$CO_2H$, or —$CH_2OH$;
$R^{20}$ is $C_1$-$C_6$-alkyl, aryl or aryl-$C_1$-$C_2$-alkyl;
$R^{21}$ is H, —$NO_2$, —$NH_2$, —OH or —$OCH_3$;
$R^{23}$ is (a) phenyl, unsubstituted or substituted with one or two substituents selected from halo, —$CH_3$ and —$CF_3$, at least one or which occupies an ortho-position;
(b) heteroaryl, selected from the group consisting of furan-2-yl, thiophen-2-yl, benzo[b]furan-2-yl, benzo[b]thiophene-2-yl, furan-3-yl, thiophen-3-yl, and oxazol-5-yl, unsubstituted or substituted with one or two substituents selected from halo, —CH$_3$ and CF$_3$ wherein at least one of the substituents is located adjacent to the carbonyl substituent or to a ring heteroatom or both;
(c) C$_3$-C$_6$-alkyl;
(d) C$_3$-C$_7$-cycloalkyl, unsubstituted or substituted at the 1- or 2-position or both with one to three substituents selected from halo, —CH$_3$ and —CH$_2$CH$_3$;
(e) C$_7$-C$_8$-bi- or tricycloalkyl;
(f) saturated 5- or 6-membered heterocyclyl linked through a carbon atom and containing one or two heteroatoms selected from oxygen and sulfur selected from the group consisting of tetrahydrofuroyl, 1,3-dithiolane, and 1,3-dithiane.

R$^{24}$ is H, or R$^{25}$,

R$^{25}$ is (a) phenyl unsubstituted or substituted with 1 or 2 substituents selected from the group consisting of halo, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, —COOR$^4$, C$_3$-C$_7$-cycloalkyl, and C$_3$-C$_{10}$-alkenyl, (b) C$_1$-C$_6$-alkyl, C$_2$-C$_6$-alkenyl or C$_2$-C$_6$-alkynyl each of which is unsubstituted or substituted with one or more substituents selected from the group consisting of aryl, C$_3$-C$_7$-cycloalkyl, halo, —OH, —O—C$_1$-C$_4$-alkyl, —NH$_2$, —NH(-C$_1$-C$_4$-alkyl), —N(C$_1$-C$_4$-alkyl)$_2$, —NH—SO$_2$R$^4$, —COOR$^4$, —SO$_2$NHR$^9$, and —S—C$_1$-C$_4$-alkyl, (c) an unsubstituted, monosubstituted or disubstituted aromatic 5 or 6 membered ring comprising one or two heteroatoms selected from the group consisting of N, O, and S, and wherein the substituents are members selected from the group consisting of —OH, —SH, C$_1$-C$_4$-alkyl, C$_1$-C$_4$-alkyloxy, —CF$_3$, —COOR$^4$, halo, and NO$_2$, or (d) C$_3$-C$_7$-cycloalkyl unsubstituted or substituted with one or more substituents selected from the group consisting of C$_1$-C$_4$-alkyl, —O—C$_1$-C$_4$-alkyl, —S—C$_1$-C$_4$-alkyl, —OH, —COOR$^4$, perfluoro—C$_1$-C$_4$-alkyl, halo;

V is
(a) H,
(b) C$_1$-C$_5$-alkoxy,
(c) C$_1$-C$_5$-alkyl,
(d) hydroxy,
(e) C$_1$-C$_5$-alkyl-S(O)$_p$,
(f) —CN,
(g) —NO$_2$,
(h) —NR$^9$R$^{10}$,
(i) C$_1$-C$_5$-alkyl-CONR$^9$R$^{10}$,
(j) —CONR$^9$R$^{10}$
(k) —CO$_2$R$^9$,
(l) C$_1$-C$_5$-alkyl-carbonyl,
(m) CF$_3$,
(n) halogen,
(o) hydroxy-C$_1$-C$_4$-alkyl-,
(p) carboxy-C$_1$-C$_4$-alkyl-,
(q) —1H-tetrazol-5-yl,
(r) —NH—SO$_2$CF$_3$,
(s) aryl,
(t) C$_1$-C$_5$-alkyl-CO$_2$R$^9$,
(u) aryloxy,
(v) aryl-C$_1$-C$_3$-alkoxy,
(w) aryl-C$_1$-C$_3$-alkyl,
(x) carboxyphenyl,
(y) heteroaryl,
(z) 2-oxazolin-2-yl unsubstituted or bearing one or more C$_1$-C$_4$-alkyl substituents,
(aa) —(CH$_2$)$_t$OCOR$^{25}$,
(bb) —(CH$_2$)$_t$OCONR$^{24}$R$^{25}$,
(cc) —(CH$_2$)$_t$NR$^{24}$COR$^{25}$,
(dd) —(CH$_2$)$_t$NR$^{24}$CO$_2$R$^{25}$,
(ee) —(CH$_2$)$_t$NR$^{24}$CONR$^{24}$R$^{25}$,
(ff) —(CH$_2$)$_t$NR$^{24}$CON(CH$_2$CH$_2$)$_2$L,
(gg) —(CH$_2$)$_t$OCON(CH$_2$CH$_2$)$_2$L,
(hh) —N(CH$_2$CH$_2$)$_2$L,
(ii) —C$_1$-C$_5$-alkyl-CON(CH$_2$CH$_2$)$_2$L, or
(jj) —CON(CH$_2$CH$_2$)L;
t is 0, 1 or 2; and
L is a bond, —CH$_2$—, —O—, —S(O)$_p$— or —NR$^9$—, wherein heteroaryl is selected from the group consisting of pyridine, pyrimidine, pyrazine, triazine, furan, thiophene, oxazole, thiazole, imidazole, triazole and thiadiazole, which is unsubstituted or fused to a benzo group and wherein the mono- or bicyclic system can be unsubstituted or substituted with one or two substituents selected from the group consisting of C$_{1-4}$ alkyl, C$_{1-4}$ alkoxy, C$_{1-4}$ alkylthio, —CF$_3$, halo, —NO$_2$, —CN, —OH, —NH$_2$, —NH(C$_{1-4}$ alkyl), —N(C$_{1-4}$ alkyl)$_2$, C$_{1-4}$ alkoxycarbonyl and —CO$_2$H.

2. The compound of claim 1 or a pharmaceutically acceptable salt thereof wherein X is —N(R$^7$)— wherein R$^7$ and R$^8$ are joined to form a ring such that R$^7$-R$^8$ is —Y—(CH$_2$)$_n$—Z—.

3. The compound of claim 2, or a pharmaceutically acceptable salt thereof wherein Y is a single bond, C(R$^{14}$)(R$^{15}$) or CO; Z is a single bond; n=1 or 2; and A, B, C and D are each —CH=;
R$^1$ is —SO$_2$NHCOR$^{23}$, —SO$_2$NHCO$_2$R$^{20}$, —SO$_2$NHCONHR$^{20}$ or 1H-tetrazol-5-yl;
R$^{2a}$, R$^{2b}$, R$^{3a}$ and R$^{3b}$ are independently H, C$_1$-C$_4$-alkyl, C$_1$-C$_4$-alkoxy or halo;
R$^6$ is C$_1$-C$_6$-alkyl, C$_2$-C$_6$-alkenyl, C$_2$-C$_6$-alkynyl, C$_3$-C$_7$-cycloalkyl, or C$_3$-C$_7$-cycloalkyl-C$_1$-C$_3$-alkyl; and
V is H, C$_1$-C$_5$-alkyl, C$_1$-C$_5$-alkoxy, —CF$_3$, halo, —NO$_2$, —NR$^9$R$^{10}$, —NR$^{24}$COR$^{25}$, —NR$^{24}$CO$_2$R$^{25}$, —NR$^{24}$CONR$^{24}$R$^{25}$, —NR$^{24}$CON(CH$_2$CH$_2$)$_2$L, —CONR$^9$R$^{10}$, —CON(CH$_2$CH$_2$)$_2$L, or —CO(C$_1$-C$_5$-alkyl);

4. The compound of claim 3 or a pharmaceutically acceptable salt thereof which is:
1-[N-[[2'-[N-(2-chlorobenzoyl)sulfamoyl]biphenyl-4-yl]methyl]-N-pentylcarbamoyl]indoline;
1-[N-[[2'-[N-(2-chlorobenzoyl)sulfamoyl]biphenyl-4-yl]methyl]-N-pentylcarbamoyl]-1,2,3,4-tetrahydroquinoline;
1-[N-butyl-N-[[2'-[N-(2-chlorobenzoyl)sulfamoyl]biphenyl-4-yl]methyl]carbamoyl]-1,2,3,4-tetrahydroquinoline;
1-[N-butyl-N-[[2'-[N-(2-chlorobenzoyl)sulfamoyl]biphenyl-4-yl]methyl]carbamoyl]-3,4-dihydro-2(1H)quinolinone.
1-[N-[[2'-[N-(t-butoxycarbonyl)sulfamoyl]biphenyl-4-yl]methyl]-N-butylcarbamoyl]-1,2,3,4-tetrahydroquinoline;
1-[N-pentyl-N-[[2'-(1H-tetrazol-5-yl)biphenyl-4-yl]methyl]carbamoyl]-1,2,3,4-tetrahydroquinoline;
ethyl 1-[N-[[2'-[N-(2-chlorobenzoyl)sulfamoyl]biphenyl-4-yl]methyl]-N-pentylcarbamoyl]-1,2,3,4-tetrahydroquinoline-2-carboxylate;
1-[N-[[2'-[N-(2-chlorobenzoyl)sulfamoyl]biphenyl-4-yl]methyl]-N-pentylcarbamoyl]-7-nitro-1,2,3,4-tetrahydroquinoline;

7-amino-1-[N-[[2'-[N-(2-chlorobenzoyl)sulfamoyl]-biphenyl-4-yl]methyl]-N-pentylcarbamoyl]-1,2,3,4-tetrahydroquinoline; or 7-(butyrylamino)-1-[N-[[2'-[N-(2-chlorobenzoyl)sulfamoyl]biphenyl-4-yl]methyl]-N-pentylcarbamoyl]-1,2,3,4-tetrahydroquinoline.

5. The compound of claim 1 or a pharmaceutically acceptable salt thereof wherein X is —N($R^7$)— and $R^7$ and $R^8$ are joined to form a ring such that $R^7$—$R^8$ is —Y—$(CH_2)_n$—Z wherein Y is a single bond; Z is O, N($R^{16}$), S, —$CF_2$—, —C($R^{14}$)($R^{15}$)— or —C(O)—; n is 2;

A, B, C and D are each —CH=
$R^1$ is —$SO_2NHCOR^{23}$, —$SO_2NHCO_2R^{20}$, —$SO_2NHCONHR^{20}$ or 1H-tetrazol-5-yl;
$R^{2a}$, $R^{2b}$, $R^{3a}$ and $R^{3b}$ are independently H, $C_1$–$C_4$-alkyl, $C_1$–$C_4$-alkoxy or halo;
$R^6$ is $C_1$–$C_6$-alkyl, $C_2$–$C_6$-alkenyl, $C_2$–$C_6$-alkynyl, $C_3$–$C_7$-cycloalkyl, or $C_3$–$C_7$-cycloalkyl-$C_1$–$C_3$-alkyl; and
V is H, $C_1$–$C_5$-alkyl, $C_1$–$C_5$-alkoxy, —$CF_3$, or halo.

6. The compound of claim 5 or a pharmaceutically acceptable salt thereof which is:

1-[N-[[2'-[N-(2-chlorobenzoyl)sulfamoyl]biphenyl-4-yl]methyl]-N-pentylcarbamoyl]-3,4-dihydro-4(1H)quinolinone;

4-[N-[[2'-[N-(2-chlorobenzoyl)sulfamoyl]biphenyl-4-yl]methyl]-N-pentylcarbamoyl]-3,4-dihydro-2H-1,4-benzothiazine;

4-[N-[[2'-[N-(2-chlorobenzoyl)sulfamoyl]biphenyl-4-yl]methyl]-N-pentylcarbamoyl]-3,4-dihydro-2H-1,4-benzoxazine;

1-acetyl-4-[N-[[2'-[N-(2-chlorobenzoyl)sulfamoyl]-biphenyl-4-yl]methyl]-N-pentylcarbamoyl]-1,2,3,4-tetrahydroquinoxaline;

1-[N-[[2'-[N-(2-chlorobenzoyl)sulfamoyl]biphenyl-4-yl]methyl]-N-pentylcarbamoyl]-4,4-difluoro-1,2,3,4-tetrahydroquinoline; or 1-[N-[[2'-[N-(2-chlorobenzoyl)sulfamoyl]biphenyl-4-yl]methyl]-N-pentylcarbamoyl]-4-methyl-1,2,3,4-tetrahydroquinoline.

7. The compound of claim 1 or a pharmaceutically acceptable salt thereof wherein $R^7$ and $R^8$ joined together are

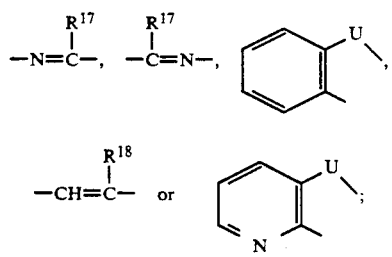

A, B, C and D are each —CH= or —N=,
$R^1$ is —$SO_2NHCOR^{23}$, —$SO_2NHCO_2R^{20}$, —$SO_2NHCONHR^{20}$ or 1H-tetrazol-5-yl;
$R^{2a}$, $R^{2b}$, $R^{3a}$ and $R^{3b}$ are independently H, $C_1$–$C_4$-alkyl, $C_1$–$C_4$-alkoxy or halo;
$R^6$ is $C_1$–$C_6$-alkyl, $C_2$–$C_6$-alkenyl, $C_2$–$C_6$-alkynyl, $C_3$–$C_7$-cycloalkyl, or $C_3$–$C_7$-cycloalkyl-$C_1$–$C_3$-alkyl; and
V is H, $C_1$–$C_5$-alkyl, $C_1$–$C_5$-alkoxy, —$CF_3$, or halo.

8. The compound of claim 7 or a pharmaceutically acceptable salt thereof which is:

10-[N-[[2'-[N-(2-chlorobenzoyl)sulfamoyl]biphenyl-4-yl]methyl]-N-pentylcarbamoyl]acridan;

10-[N-[[2'-[N-(2-chlorobenzoyl)sulfamoyl]biphenyl-4-yl]methyl]-N-pentylcarbamoyl]-9(10H)-acridone;

10-[N-[[2'-[N-(2-chlorobenzoyl)sulfamoyl]biphenyl-4-yl]methyl]-N-pentylcarbamoyl]phenoxazine;

3-chloro-1-[N-[[2'-[N-(2-chlorobenzoyl)sulfamoyl]-biphenyl-4-yl]methyl]-N-pentylcarbamoyl]indazole;

1-[N-[[2'-[N-(2-chlorobenzoyl)sulfamoyl]biphenyl-4-yl]methyl]-N-pentylcarbamoyl]-3-methylindole; or 1-[N-[[2'-[N-(2-chlorobenzoyl)sulfamoyl]biphenyl-4-yl]methyl]-N-pentylcarbamoyl]-2-methylbenzimidazole.

9. The compound of claim 1 or a pharmaceutically acceptable salt thereof wherein X is —N($R^7$)— wherein $R^7$ is aryl, heteroaryl, aryl-$C_1$–$C_6$-alkyl, or $C_1$–$C_6$-alkyl.

10. The compound of claim 9 or a pharmaceutically acceptable salt thereof wherein
A, B, C and D are each —CH= or —N=;
$R^1$ is —$SO_2NHCOR^{23}$, —$SO_2NHCO_2R^{20}$, —$SO_2NHCONHR^{20}$ or -1H-tetrazol-5-yl;
$R^{2a}$, $R^{2b}$, $R^{3a}$, $R^{3b}$ are independently H, $C_1$–$C_4$-alkyl, $C_1$–$C_4$-alkoxy, or halo;
$R^6$ is $C_1$–$C_6$-alkyl, $C_2$–$C_6$-alkenyl, $C_2$–$C_6$-alkynyl, $C_3$–$C_7$-cycloalkyl; or $C_3$–$C_7$-cycloalkyl-$C_1$–$C_3$-alkyl; and
$R^{7\text{-}8}$ is H, halo, or —$CF_3$
V is H, $C_1$–$C_5$-alkyl, $C_1$–$C_5$-alkoxy, $CF_3$, halo, —$NO_2$, —$NR^9R^{10}$, —$NR^{24}COR^{25}$, —$NR^{24}CO_2R^{25}$, —$NR^{24}CONR^{24}R^{25}$, —$NR^{24}CON(CH_2CH_2)_2L$, —$CONR^9R^{10}$, —$CON(CH_2CH_2)_2L$, or —$CO(C_1$–$C_5$-alkyl);

11. The compound of claim 10 or a pharmaceutically acceptable salt thereof which is:

1-butyl-1-[[2'-N-(2-chlorobenzoyl)sulfamoyl]biphenyl-4-yl]methyl]-3-phenyl-3-(2-pyridyl)urea;

1-[[2'-[N-(2-chlorobenzoyl)sulfamoyl]biphenyl-4-yl]methyl]-1-pentyl-3-phenyl-3-(2-pyridyl)urea;

1-benzyl-3-butyl-3-[[2'-[N-(2-chlorobenzoyl)sulfamoyl]-biphenyl-4-yl]methyl]-1-phenylurea;

1-benzyl-3-[[2'-[N-(2-chlorobenzoyl)sulfamoyl]biphenyl-4-yl]methyl]-3-pentyl-1-phenylurea;

1-butyl-1-[[2'-[N-(2-chlorobenzoyl)sulfamoyl]biphenyl-4-yl]methyl]-3-methyl-3-[2-(trifluoromethyl)phenyl]urea;

1-methyl-3-pentyl-3-[[2'-(1H-tetrazol-5-yl)biphenyl-4-yl]methyl]-1-[2-(trifluoromethyl)phenyl]urea;

1-[[2'-[N-(2-chlorobenzoyl)sulfamoyl]biphenyl-4-yl]methyl]-3-methyl-1-pentyl-3-[2-(trifluoromethyl)-phenyl]urea;

1-[[2'-[N-(2-chlorobenzoyl)sulfamoyl]biphenyl-4-yl]methyl]-3-methyl-1-pentyl-3-phenylurea;

1-[[2'-[N-(2-chlorobenzoyl)sulfamoyl]biphenyl-4-yl]methyl]-1-pentyl-3,3-diphenylurea;

1-[[2'-[N-(2-chlorobenzoyl)sulfamoyl]biphenyl-4-yl]methyl]-3-(3-chloro-2-pyridyl)-1-pentyl-3-phenylurea;

1-[[2'-[N-(2-chlorobenzoyl)sulfamoyl]biphenyl-4-yl]methyl]-3-(2-chlorophenyl)-1-pentyl-3-(2-pyridyl)urea;

1-benzyl-3-[[2'-[N-(2-chlorobenzoyl)sulfamoyl]biphenyl-4-yl]methyl]-3-pentyl-1-[2-(trifluoromethyl)-phenyl]urea;

1-[[2'-[N-(2-chlorobenzoyl)sulfamoyl]biphenyl-4-yl]methyl]-3-[2-chloro-5-(valerylamino)phenyl]-3-methyl-1-pentylurea;

1-[[2'-[N-(2-chlorobenzoyl)sulfamoyl]biphenyl-4-yl]methyl]-3-(2-chlorophenyl)-3-methyl-1-pentylurea;

1-butyl-1-[[2'-[N-(2-chlorobenzoyl)sulfamoyl]-5'-propylbiphenyl-4-yl]methyl]-3-methyl-3-[2-(trifluoromethyl)phenyl]urea;

1-[[2'-[N-(2-chlorobenzoyl)sulfamoyl]-5'-ethylbiphenyl-4-yl]methyl]-3-[2-chloro-5-(propionylamino)phenyl]-3-methyl-1-pentylurea;

1-[[2'-[N-(t-butoxycarbonyl)sulfamoyl]biphenyl-4-yl]methyl]-1-butyl-3-[2-chloro-5-(valerylamino)phenyl]-3-methylurea;

1-[[2'-[N-(n-butoxycarbonyl)sulfamoyl]biphenyl-4-yl]methyl]-3-[2-chloro-5-(valerylamino)phenyl]-3-methyl-1-pentylurea;

1-[[2'-[N-(N-butylcarbamoyl)sulfamoyl]biphenyl-4-yl]methyl]-3-[2-chloro-5-(valerylamino)phenyl]-3-methyl-1-pentylurea;

1-[5-(N-butylcarbamoyl)-2-chlorophenyl]-3-[[2'-[N-(2-chlorobenzoyl)sulfamoyl]biphenyl-4-yl]methyl]-1-methyl-3-pentylurea; or 1-[[2'-[N-(3-chloro-2-furoyl)sulfamoyl]biphenyl-4-yl]methyl]-3-methyl-1-pentyl-3-[2-(trifluoromethyl)phenyl]urea.

12. The compound of claim 1 or a pharmaceutically acceptable salt thereof wherein X is —O—.

13. The compound of claim 12 or a pharmaceutically acceptable salt thereof wherein
   $R^1$ is —SO$_2$NHCOR$^{23}$, —SO$_2$NHCO$_2$R$^{20}$, —SO$_2$NHCONHR$^{20}$ or -1H-tetrazol-5-yl;
   $R^{2a}$, $R^{2b}$, $R^{3a}$, $R^{3b}$ are independently H, C$_1$–C$_4$-alkyl, C$_1$–C$_4$-alkoxy, or halo;
   $R^6$ is C$_1$–C$_6$-alkyl, C$_2$–C$_6$-alkenyl, C$_2$–C$_6$-alkynyl, C$_3$–C$_7$-cycloalkyl; or C$_3$–C$_7$-cycloalkyl C$_1$–C$_3$-alkyl; and 14. The compound of claim 13 or a pharmaceutically acceptable salt thereof which is:
2-(trifluoromethyl)phenyl N-butyl-N-[[2'-[N-(2-chlorobenzoyl)sulfamoyl]biphenyl-4-yl]methyl]carbamate; or
2-(trifluoromethyl)phenyl N-[[2'-[N-(2-chlorobenzoyl)sulfamoyl]biphenyl-4-yl]methyl]-N-pentylcarbamate.

15. The compound of claim 1 or a pharmaceutically acceptable salt thereof wherein R$^6$ is heteroaryl and X is —O— or NR$^7$.

16. The compound of claim 15 or a pharmaceutically acceptable salt thereof wherein R$^6$ is pyridyl or pyrimidyl.

17. The compound of claim 16 or a pharmaceutically acceptable salt thereof which is:
1-[[2'-[N-(2-chlorobenzoyl)sulfamoyl]biphenyl-4-yl]methyl]-3-methyl-1-(2-methyl-4-pyridyl)-3-[2-(trifluoromethyl)phenyl]urea;

1-[[2'-[N-(2-chlorobenzoyl)sulfamoyl]biphenyl-4-yl]methyl]-3-methyl-1-(2,6-dimethyl-4-pyrimidyl)-3-[2-(trifluoromethyl)phenyl]urea;

1-(2-ethyl-4-pyridyl)-3-methyl-1-[[2'-(1H-tetrazol-5-yl)biphenyl-4-yl]methyl]-3-[2-(trifluoromethyl)phenyl]urea;

1-[[2'-[N-(2-chlorobenzoyl)sulfamoyl]-5'-ethylbiphenyl-4-yl]methyl]-3-[2-chloro-5-(propionylamino)phenyl]-3-methyl-1-(2-methyl-4-pyridyl)urea; or 2-(trifluoromethyl)phenyl N-[[2'-[N-(2-chlorobenzoyl)sulfamoyl]biphenyl-4-yl]methyl]-N-(2-methyl-4-pyridyl)carbamate.

18. A pharmaceutical composition useful in the treatment of hypertension which comprises a pharmaceutically acceptable carrier and a pharmaceutically effective amount of a compound of claim 1.

19. The composition of claim 6 which includes another antihypertensive selected from a diuretic selected from hydrochlorothiazide, chlorothiazide, chlorthalidone, methyclothiazide, furosemide, ethacrynic acid, triamterene, amiloride and spironolactone; a calcium channel blocker, selected from diltiazem, felodipine, nifedipine, nitrendipine and verapamil; a β-adrenergic antagonist selected from timolol, atenolol, metoprolol, propanolol, nadolol and pindolol; an angiotensin converting enzyme inhibitor selected from enalapril, lisinopril, captopril, ramipril, quinapril and zofenopril; a renin inhibitor selected from A-69729 and FK 744; an α-adrenergic antagonist selected from prazosin, doxazosin, and terazosin; a sympatholytic agent selected from methyldopa, clonidine and guanabenz; the antriopeptidase inhibitor, UK-79300; the serotonin antagonist, ketanserin; the A$_2$-adenosine receptor agonist CGS 22492C; a potassium channel agonist selected from pinacidil and cromakalim; or another antihypertensive drug selected from reserpine, minoxidil, guanethidine, hydralazine hydrochloride and sodium nitroprusside; or combinations of the above-named drugs.

20. A method of treating hypertension which comprises administering to a patient in need of such treatment a pharmaceutically effective amount of a compound of claim 1.

21. An ophthalmological formulation for the treatment of ocular hypertension comprising an opthalmologically acceptable carrier and an effective ocular antihypertensive amount of a compound of claim 1.

22. A method of treating ocular hypertension comprising administering to a patient in need of such treatment an effective ocular antihypertensive amount of a compound of claim 1.

* * * * *